United States Patent
Pelrine et al.

(10) Patent No.: US 6,876,135 B2
(45) Date of Patent: Apr. 5, 2005

(54) MASTER/SLAVE ELECTROACTIVE POLYMER SYSTEMS

(75) Inventors: Ronald E. Pelrine, Boulder, CO (US); Roy D. Kornbluh, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 266 days.

(21) Appl. No.: 10/161,574

(22) Filed: May 31, 2002

(65) Prior Publication Data

US 2003/0067245 A1 Apr. 10, 2003

Related U.S. Application Data

(60) Provisional application No. 60/327,722, filed on Oct. 5, 2001.

(51) Int. Cl.[7] .............................................. H01L 41/08

(52) U.S. Cl. ...................... 310/339; 310/317; 310/800

(58) Field of Search ............................... 310/317, 338, 310/339, 800

(56) References Cited

U.S. PATENT DOCUMENTS

| | | | | | |
|---|---|---|---|---|---|
| 4,190,336 | A | * | 2/1980 | Frank et al. | 396/248 |
| 4,400,634 | A | | 8/1983 | Micheron | 300/400 |
| 4,843,275 | A | | 6/1989 | Radice | 310/334 |
| 4,849,668 | A | * | 7/1989 | Crawley et al. | 310/328 |
| 4,885,783 | A | | 12/1989 | Whitehead et al. | 381/191 |
| 5,918,502 | A | | 7/1999 | Bishop | 73/172 |
| 5,977,685 | A | | 11/1999 | Kurita et al. | 310/311 |
| 6,048,622 | A | | 4/2000 | Hagood, IV et al. | 428/461 |
| 6,060,811 | A | | 5/2000 | Fox et al. | 310/311 |
| 6,486,589 | B1 | * | 11/2002 | Dujari et al. | 310/331 |
| 6,528,928 | B1 | * | 3/2003 | Burns et al. | 310/339 |
| 6,700,314 | B2 | * | 3/2004 | Cuhat et al. | 310/334 |

FOREIGN PATENT DOCUMENTS

EP 0 522 882 A2 1/1993 ............ A43B/3/00

OTHER PUBLICATIONS

Ajluni, Cheryl, "Pressure Sensors Strive to Stay on Top, New Silicon Micromachining Techniques and Designs Promise Higher Performance", *Electronic Design—Advanced Technology Series*, Oct. 3, 1994, pp. 67–74.

Ashley, S., "Smart Skis and Other Adaptive Structures", *Mechanical Engineering*, Nov. 1995, pp. 77–81.

Bar–Cohen, Yoseph, JPL, *WorldWide ElectroActive Polymers, EAP (Artificial Muscles) Newsletter*, vol. 1, No. 1, Jun. 1999.

(Continued)

*Primary Examiner*—Thomas M. Dougherty
(74) *Attorney, Agent, or Firm*—Beyer Weaver & Thomas LLP

(57) ABSTRACT

The present invention relates to improved devices, systems and methods that convert between electrical and mechanical energy. An electroactive polymer transducer converts between electrical and mechanical energy. An active area is a portion of an electroactive polymer transducer. The active area comprises a portion of an electroactive polymer and at least two electrodes that provide or receive electrical energy to or from the portion. The present invention relates to transducers and devices comprising multiple active areas that are in electrically communication. More specifically, the present invention relates to master/slave arrangements for multiple active areas disposed on one or more electroactive polymers. In a master/slave arrangement, a first active area deflects (a 'master'), and a second active area reacts (a 'slave'). Communication electronics in electrical communication with electrodes for the first active area and in electrical communication with electrodes for the second active area transfer electrical energy between the two active areas.

31 Claims, 15 Drawing Sheets

OTHER PUBLICATIONS

Cheng, Z.-Y., T.-B. Xu, V. Bharti, S. Wang, and Q. M. Zhang, "Transverse Strain Responses In The Electrostrictive Poly(Vinylidene Fluoride–Trifluorethylene) Copolymer," *Appl. Phys. Lett.* vol. 74, No. 13, pp. 1901–1903, Mar. 29, 1999.

Kornbluh, R., Pelrine, R., Eckerie, J., Joseph, J., "Electrostrictive Polymer Artificial Muscle Actuators", IEEE International Conference on Robotics and Automation, Leuven, Belgium, 1998.

Ktech's PVDF Sensors, http://www.ktech.com/pvdf.htm, Jun. 6, 2001, pp. 1–5.

Pei et al., "Improved Electroactive Polymers", U.S. Appl. No. 09/619,847, filed Jul. 20, 2000, 70 pages.

Pelrine, R., R. Kornbluh, and Q. Pei. "Electroactive Polymer Transducers And Actuators", U.S. Appl. No. 09/620,025, filed Jul. 20, 2001, 58 pages.

Pelrine, R. and Kornbluh, "Electroactive Polymer Devices", U.S. Appl. No. 09/619,846, filed Jul. 20, 2000, 67 pages.

Pelrine et al., "Electroactive Polymer Generators", U.S. Appl. No. 09/619,848, filed Jul. 20, 2000, 69 pages.

Pelrine, R., R. Kornbluh, and J. Joseph, FY 1998 *Final Report on Artifical Muscle for Small Robots*, ITAD–3482–FR–99–36, SRI International, Menlo Park, California, 1999.

Pelrine, R., R. Kornbluh, Q. Pei, and J. Joseph, "High Speed Electrically Actuated Elastomers with Over 100% Strain," *Science*, vol. 287, No. 5454, pp. 1–21, 2000.

Pelrine, R., R. Kornbluh, and G. Kofod, "High Strain Actuator Materials Based on Dielectric Elastomers," submitted to *Advanced Materials* (May 2000).

Pelrine, R., Roy Kornbluh, Jose Joseph, Qibing Pei, Seiki Chiba "Recent Progress in Artificial Muscle Micro Actuators," SRI International, Tokyo, 1999 MITI/NEEDOIMNIC, 1999.

Treloar, L.R.G., "Mechanics of Rubber Elasticity," *J Polymer Science, Polymer Symposium*, No. 48, pp. 107–123, 1974.

Uchino, K. 1986. "Electrostrictive Actuators: Materials and Applications," *Ceramic Bulletin*, 65(4), pp. 647–652, 1986.

Winters, J., "Muscle as an Actuator for Intelligent Robots", Robotics Research: Trans. Robotics International of SME, Scottsdale, AZ (Aug. 18–21, 1986).

Zhenyi, M., J.I, Scheinbeim, J.W. Lee, and B.A. Newman. 1994. "High Field Electrostrictive Response of Polymers," *Journal of Polymer Sciences, Part B—Polymer Physics*, vol. 32, pp. 2721–2731, 1994.

Pelrine et al., "Monolithic Electroactive Polymers", U.S. Appl. No. 09/779,203, filed Feb. 7, 2001, 47 pages.

Kornbluh, et al., "Electroactive Polymer Sensors", U.S. Appl. No. 10/007,705, filed Dec. 6, 2001, 70 pages.

Pelrine et al., "Biologically Powered Electroactive Polymer Generators", U.S. Appl. No. 09/792,877, filed Feb. 23, 2001, 93 pages.

Roy D. Kornbluh and Ronald E. Pelrine, "Variable Stiffness Electroactive Polymer Systems", U.S. Appl. No. 10/053,511, filed Jan. 16, 2002, 64 pages.

John Kymissis et al., "Parasitic Power Harvesting in Shoes", Physics and Media Group, MIT Media Laboratory E15–410, Cambridge MA, Oct. 19, 1998, pp. 132–139.

* cited by examiner

MASTER/SLAVE ELECTROACTIVE POLYMER SYSTEMS

CROSS-REFERENCE TO RELATED APPLICATION

This application claims priority under 35 U.S.C. §119(e) from U.S. Provisional Patent Application No. 60/327,722 filed on Oct. 5, 2001, which is incorporated by reference for all purposes.

U.S. GOVERNMENT RIGHTS

This application was made in part with government support under contract number DAAG55-98-K-0001 awarded by the United States Army Research Office and Defense Advanced Research Project Agency. The government has certain rights in the invention.

BACKGROUND OF THE INVENTION

The present invention relates generally to electroactive polymer systems and methods that convert between electrical energy and mechanical energy. More particularly, the present invention relates to electroactive polymers, transducers and devices having multiple active areas that communicate electrical energy between them. The present invention also relates to methods of using electroactive polymers having multiple active areas.

In many applications, it is desirable to convert between electrical energy and mechanical energy. Exemplary applications requiring conversion from electrical to mechanical energy include robotics, pumps, speakers, sensors, microfluidics, shoes, general automation, disk drives, and prosthetic devices. These applications include one or more transducers that convert electrical energy into mechanical work—on a macroscopic or microscopic level. Common actuator technologies, such as electromagnetic motors and solenoids, are not suitable for many applications, e.g., when the required device size is small (e.g., micro or mesoscale machines) or the weight or complexity must be minimized. Exemplary applications requiring conversion from mechanical to electrical energy include sensors and generators. These applications include one or more generators that convert mechanical energy into electrical energy. Common electric generator technologies, such as electromagnetic generators, are not suitable for many of these applications, e.g., when the required device size is small (e.g., in a person's shoe). These transducer technologies are also not ideal when a large number of devices must be integrated into a single structure or under various performance conditions such as when high power density output is required at relatively low frequencies.

Several 'smart materials' have been used to convert between electrical and mechanical energy with limited success. These smart materials include piezoelectric ceramics, shape memory alloys and magnetostrictive materials. However, each smart material has a number of limitations that prevent its broad usage. Certain piezoelectric ceramics, such as lead zirconium titanate (PZT), have been used to convert electrical to mechanical energy. While having suitable efficiency for a few applications, these piezoelectric ceramics are typically limited to a strain below about 1.6 percent and are often not suitable for applications requiring greater strains than this. In addition, the high density of these materials often eliminates them from applications requiring low weight. Irradiated polyvinylidene fluoride (PVDF) with various co-polymers is an electroactive polymer reported to have a strain of up to 4 percent when converting from electrical to mechanical energy. Similar to the piezoelectric ceramics, PVDF is often not suitable for applications requiring strains greater than 4 percent. Shape memory alloys, such as nitinol, are capable of large strains and force outputs. These shape memory alloys have been limited from broad use due to unacceptable energy efficiency, poor response time and prohibitive cost.

Typically, the above transducer technologies comprise a single active area for converting between mechanical and electrical energy; and a transducer is therefor dedicated to a single function. For a mechanical output application for example, a single piezoelectric ceramic is employed for actuation only. Alternatively, a single piezoelectric ceramic is typically configured solely for sensing in a sensing application. In many applications however, more advanced devices that convert between electrical and mechanical energy may be desirable.

SUMMARY OF THE INVENTION

The present invention relates to improved devices, systems and methods that convert between electrical and mechanical energy. An electroactive polymer transducer converts between electrical and mechanical energy. An active area is a portion of an electroactive polymer transducer. The active area comprises a portion of an electroactive polymer and at least two electrodes that provide or receive electrical energy to or from the portion. The present invention relates to transducers and devices comprising multiple active areas that are electrically related. More specifically, the present invention relates to master/slave arrangements for multiple active areas disposed on one or more electroactive polymers. In a master/slave arrangement, a first active area deflects (a 'master'), and a second active area reacts (a 'slave'). Communication electronics in electrical communication with electrodes for the first active area and in electrical communication with electrodes for the second active area transfer electrical energy between the two. In some cases, the master produces electrical energy and the slave may use this energy as desired by an application. For example, the slave may actuate and deflect in response to electrical power generated by the master active area.

In one aspect, the present invention relates to a device for converting between electrical and mechanical energy. The device comprises a first active area that converts between electrical energy and mechanical energy. The first active area comprises a first portion of at least one electroactive polymer and at least two first active area electrodes in electrical communication with the first portion. The device also comprises a second active area that converts between electrical energy and mechanical energy. The second active area comprises a second portion of the at least one electroactive polymer and at least two second active area electrodes in electrical communication with the second portion. The device further comprises communication electronics in electrical communication with the first active area and in electrical communication with the second active area. The communication electronics transfer at least a portion of an electrical energy change from one of the first active area and the second active area to the other of the first active area and the second active area.

In another aspect, the present invention relates to a device for converting between electrical and mechanical energy. The device comprises a first active area that converts mechanical energy to electrical energy. The first active area comprises a first portion of at least one electroactive polymer and at least two first active area electrodes in electrical communication with the first portion. The device also comprises a second active area that converts electrical energy to mechanical energy. The second active area comprises a second portion of the at least one electroactive polymer and at least two second active area electrodes in electrical communication with the second portion. The device further comprises communication electronics in electrical communication with the first active area and in electrical communication with the second active area. The communication electronics transfer at least a portion of the electrical energy generated by the first active area to the second active area.

In yet another aspect, the present invention relates to a method for using multiple electroactive polymer active areas. The method comprises deflecting a first portion of at least one electroactive polymer. The first portion is associated with a first active area. The method also comprises receiving an electrical energy change in response to the first portion deflection. The method further comprises transferring at least a portion of the electrical energy change from the first active area to a second active area.

In yet another aspect, the present invention relates to a device included in footwear for converting between electrical and mechanical energy during human bipedal motion. The device comprises a first active area that converts between electrical energy and mechanical energy. The first active area comprises a first portion of at least one electroactive polymer mounted in footwear and at least two first active area electrodes in electrical communication with the first portion. The device also comprises a second active area that converts between electrical energy and mechanical energy. The second active area comprises a second portion of the at least one electroactive polymer and at least two second active area electrodes in electrical communication with the second portion. The device further comprises communication electronics in electrical communication with the first active area and in electrical communication with the second active area. The communication electronics transfer electrical energy generated by one of the first active area and the second active area to the other of the first active area and the second active area. The device additionally comprises one or more transmission mechanisms that are designed or configured to receive mechanical energy generated during human bipedal motion and to transfer a portion of the mechanical energy to one of the first active or second active area. The transferred portion of the mechanical energy results in a deflection in the portion of the polymer corresponding to the other of the first active area and the second active area.

These and other features and advantages of the present invention will be described in the following description of the invention and associated figures.

DETAILED DESCRIPTION OF THE PREFERRED EMBODIMENTS

The present invention is described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

1. Overview

An electroactive polymer transducer converts between electrical and mechanical energy and comprises an electroactive polymer and at least two electrodes that provide or receive electrical energy to or from the polymer. The electroactive polymer transducer may be employed for one or more functions. When a suitable voltage is applied to electrodes in electrical communication with an electroactive polymer, the polymer deflects (actuation). This deflection may be used to do mechanical work. Whether or not the polymer deflects, electrical states imposed on the polymer may be used to vary the stiffness or damping provided by the polymer, which has various mechanical uses. When a previously charged electroactive polymer deflects, the electric field in the material is changes. The change in electric field may be used to produce electrical energy—for generation or sensing purposes. Thus, some functions of use for an electroactive polymer include actuation, variable stiffness or damping, generation or sensing. As described herein, an electroactive polymer transducer may be used for any electrical and mechanical energy conversion function and is not limited to the examples described herein.

An active area is a portion of an electroactive polymer transducer. The active area comprises a portion of an electroactive polymer and at least two electrodes that provide or receive electrical energy to or from the portion. The active area may be used for any of the functions described above. For actuation, the active area may be defined as having sufficient electrostatic force when a voltage is applied to enable deflection of the portion. For generation or sensing, the active area may be defined as sufficient deflection to enable a change in electrostatic force or electric field. The present invention relates to transducers and devices comprising multiple active areas. The multiple active areas may be implemented on one electroactive polymer, or multiple electroactive polymers.

Figure 1:
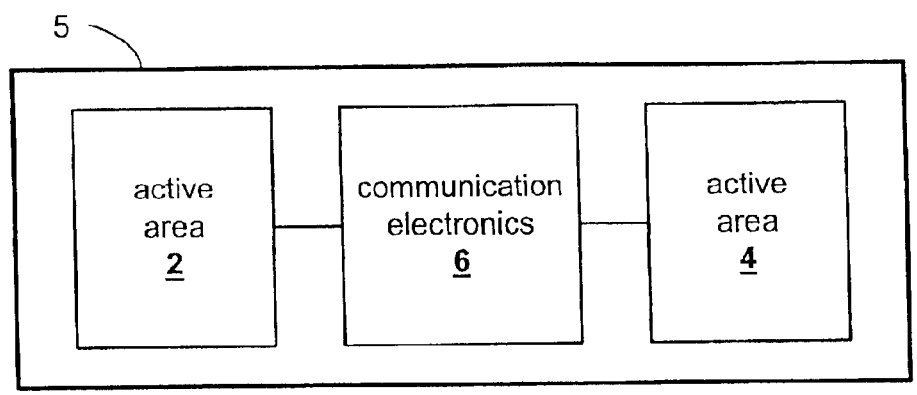
FIG. 1 illustrates a multiple active area device for converting between electrical and mechanical energy in accordance with one embodiment of the present invention.

FIG. 1 illustrates a multiple active area device 5 for converting between electrical and mechanical energy in accordance with one embodiment of the present invention. Power supply devices would be incorporated into the communication electronics. Device 5 comprises a first active area 2, a second active area 4, and communication electronics 6. Active areas 2 and 4 convert between mechanical and electrical energy. Active area 2 comprises a first portion of at least one electroactive polymer and at least two electrodes that provide or receive electrical energy to or from the first portion. Active area 4 comprises a second portion of the at least one electroactive polymer and at least two electrodes that provide or receive electrical energy to or from the second portion.

The present invention relates to master/slave arrangements for multiple active areas disposed on one or more electroactive polymers. In a master/slave arrangement, a first active area (a 'master') receives an external deflection. Communication electronics in electrical communication with electrodes for the master receive an electrical change resulting from the deflection and transfer at least a portion of this electrical change to another active area (a 'slave'). The slave may increase or decrease in electrical energy in response to deflection of the master active area.

In one master/slave arrangement, a master acting as a generator produces electrical energy with deflection. Communication electronics in electrical communication with electrodes for the master transfer at least a portion of this electrical energy to a slave. The slave may use this energy as desired by an application. For example, the slave may actuate and deflect in response to electrical power generated by the master active area.

The master active area of the master/slave system typically comprises an electroactive polymer, or portion thereof, configured to produce an electrical energy change when deflected by an external mechanical source. In one embodiment, the master acts as an electroactive polymer generator to produce electrical energy in response to the deflection. Electroactive polymer generators are further described below. The master active area also comprises at least two compliant electrodes configured to provide or receive electrical energy to or from a portion of the electroactive polymer.

The slave active area of the master/slave system typically comprises an electroactive polymer, or a portion thereof, configured to change according to at least a portion of the electrical energy change in the master. This may include an electrical state change and no deflection. Depending on the loading on the polymer and the amount of electrical energy provided to the slave, the slave may deflect in response to electrical energy and act as an electroactive polymer in actuation. Actuation of electroactive polymers is described below. In one embodiment, the slave is configured as an actuator that produces a linear or customized output deflection in response to electrical energy changes transferred from the master. The slave also comprises at least two compliant electrodes configured to provide electrical energy to the electroactive polymer.

Referring to FIG. 1, either of the active areas 2 and 4 may be a master and the other a slave (given suitable communication and control electronics). Thus, active area 2 may be used as a master to produce an electrical energy change that is provided to active area 4. Alternatively, active area 4 may be used as a master to produce an electrical energy change that is provided to active area 2.

Communication electronics 6 are in electrical communication with active area 2 and in electrical communication with active area 4. Communication electronics 6 receive electrical energy changes from one of the active areas and provide at least a portion of the electrical energy change to the other.

Figure 3A:
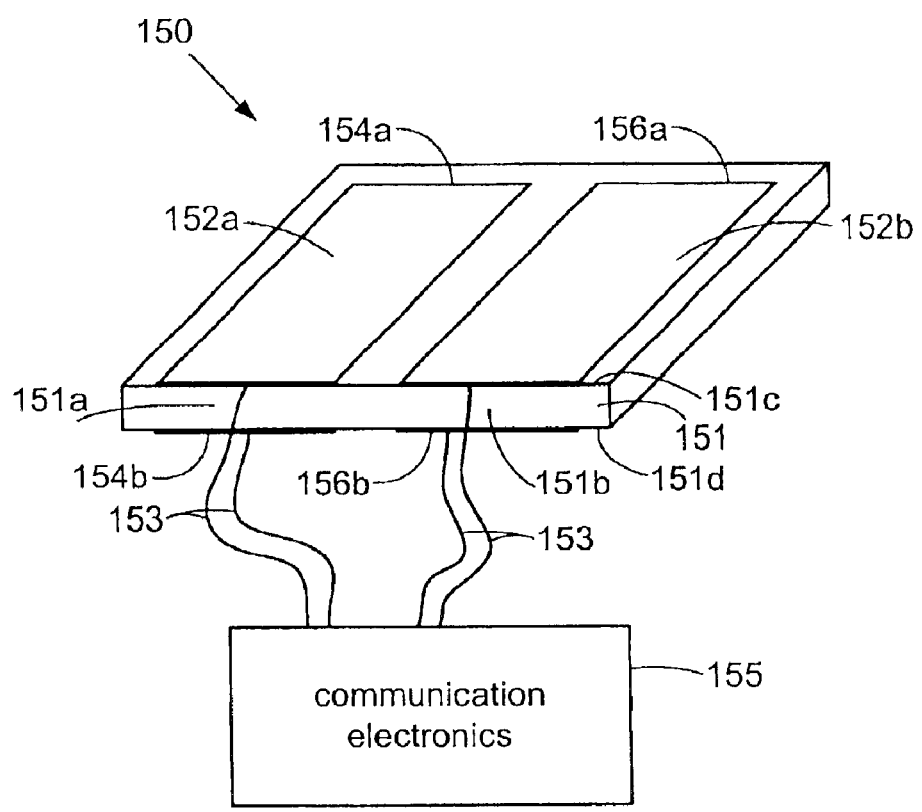
FIG. 3A illustrates a monolithic transducer comprising a plurality of active areas on a single polymer in accordance with one embodiment of the present invention.

In one embodiment, active areas 2 and 4 are arranged on a single polymer (see FIG. 3A). In another embodiment, active areas 2 and 4 are arranged on multiple polymers (see FIGS. 3B–3C). The ability to arrange multiple active areas on a single polymer or multiple polymers allows for numerous master/slave configurations.

Active areas 2 and 4 may be used in a variety of ways. For example, active area 2 may be used for actuation, generation, sensing, changing the stiffness and/or damping for a portion of a device that the active area is implemented with, or a combination thereof. Suitable electrical control also allows a single active area to be used for more than one function. For example, active area 2 may be used for actuation and variable stiffness control of a robotic limb in a robotics application. The same active area may also be used for generation that produces electrical energy based on motion of the robotic limb. Active area 4 may also be flexibly used for actuation, generation, sensing, changing stiffness, or a combination thereof. Energy generated by either active area may be provided to the other active area as desired by an application. Thus, polymers and transducers of the present invention may be used as an actuator to convert from electrical to mechanical energy, a generator to convert from mechanical to electrical energy, a sensor that detects a parameter, or a variable stiffness and/or damping device that is used to control stiffness and/or damping.

Active areas for an electroactive polymer may be easily patterned and configured using conventional electroactive polymer electrode fabrication techniques. Given the ability to pattern and flexibly use multiple active areas independently among a variety of active areas allows transducers and devices of the present invention to be used in many new applications and to be used in existing applications in new ways.

In all the figures and discussions for the present invention, it is important to note that active areas and transducers may convert between electrical energy and mechanical energy bi-directionally. Thus, any of the polymer materials, active areas, polymer configurations, transducers, and devices described herein may be a transducer for converting mechanical energy to electrical energy (generation, variable stiffness or damping, or sensing) and for converting electrical energy to mechanical energy (actuation, variable stiffness or damping, or sensing). Typically, a generator or sensor active area of the present invention comprises a polymer arranged in a manner that causes a change in electric field in response to deflection of a portion of the polymer. The change in electric field, along with changes in the polymer film area, produces a change in voltage, and hence a change in electrical energy.

Often the transducer is employed within a device that comprises other structural and/or functional elements. For example, external mechanical energy may be input into the master in some manner via one or more mechanical transmission coupling mechanisms. For example, the transmission mechanism may be designed or configured to receive biologically-generated mechanical energy and to transfer a portion of the biologically-generated mechanical energy to a portion of a polymer where the transferred portion of the biologically generated mechanical energy results in a deflection in the master. The biologically-generated mechanical energy may produce an inertial force or a direct force where a portion of the inertial force or a portion of the direct force is received by the transmission mechanism. In one embodiment, the direct force may be from a foot strike on the ground.

2. Electroactive Polymers

The transformation between electrical and mechanical energy in devices of the present invention is based on energy conversion of one or more active areas of an electroactive polymer. Electroactive polymers are capable of converting between mechanical energy and electrical energy. In some cases, an electroactive polymer may change electrical properties (for example, capacitance and resistance) with changing mechanical strain.

Figure 2A:
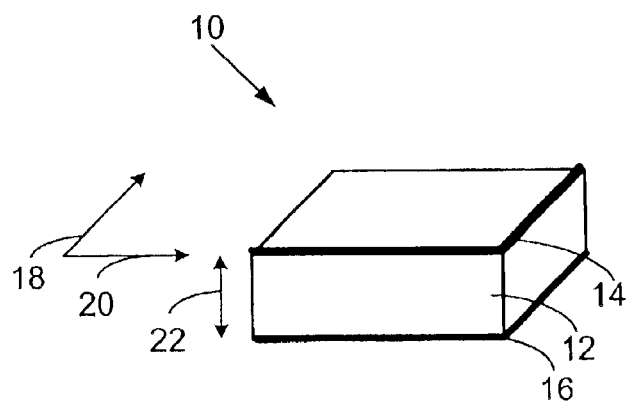
FIGS. 2A and 2B illustrate a top view of a transducer portion before and after application of a voltage, respectively, in accordance with one embodiment of the present invention.

To help illustrate the performance of an electroactive polymer in converting between electrical energy and mechanical energy, FIG. 2A illustrates a top perspective view of a transducer portion 10 in accordance with one embodiment of the present invention. The transducer portion 10 comprises a portion of an electroactive polymer 12 for converting between electrical energy and mechanical energy. In one embodiment, an electroactive polymer refers to a polymer that acts as an insulating dielectric between two electrodes and may deflect upon application of a voltage difference between the two electrodes. Top and bottom electrodes 14 and 16 are attached to the electroactive polymer 12 on its top and bottom surfaces, respectively, to provide a voltage difference across polymer 12, or to receive electrical energy from the polymer 12. Polymer 12 may deflect with a change in electric field provided by the top and bottom electrodes 14 and 16. Deflection of the transducer portion 10 in response to a change in electric field provided by the electrodes 14 and 16 is referred to as 'actuation'. Actuation typically involves the conversion of electrical energy to mechanical energy. As polymer 12 changes in size, the deflection may be used to produce mechanical work.

Figure 2B:
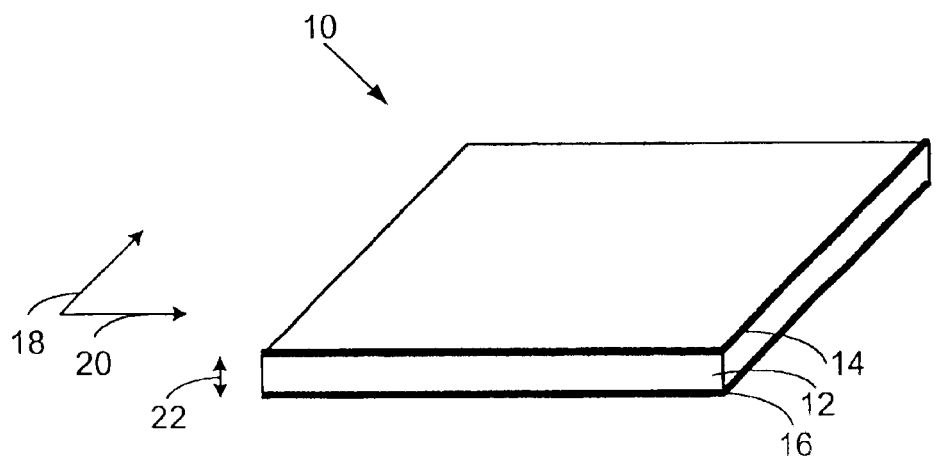

FIG. 2B illustrates a top perspective view of the transducer portion 10 including deflection. In general, deflection refers to any displacement, expansion, contraction, torsion, linear or area strain, or any other deformation of a portion of the polymer 12. For actuation, a change in electric field corresponding to the voltage difference applied to or by the electrodes 14 and 16 produces mechanical pressure within polymer 12. In this case, the unlike electrical charges produced by electrodes 14 and 16 attract each other and provide a compressive force between electrodes 14 and 16 and an expansion force on polymer 12 in planar directions 18 and 20, causing polymer 12 to compress between electrodes 14 and 16 and stretch in the planar directions 18 and 20.

Electrodes 14 and 16 are compliant and change shape with polymer 12. The configuration of polymer 12 and electrodes 14 and 16 provides for increasing polymer 12 response with deflection. More specifically, as the transducer portion 10 deflects, compression of polymer 12 brings the opposite charges of electrodes 14 and 16 closer and the stretching of polymer 12 separates similar charges in each electrode. In one embodiment, one of the electrodes 14 and 16 is ground. For actuation, the transducer portion 10 generally continues to deflect until mechanical forces balance the electrostatic forces driving the deflection. The mechanical forces include elastic restoring forces of the polymer 12 material, the compliance of electrodes 14 and 16, and any external resistance provided by a device and/or load coupled to the transducer portion 10, etc. The deflection of the transducer portion 10 as a result of an applied voltage may also depend on a number of other factors such as the polymer 12 dielectric constant and the size of polymer 12.

Electroactive polymers in accordance with the present invention are capable of deflection in any direction. After application of a voltage between the electrodes 14 and 16, the electroactive polymer 12 increases in size in both planar directions 18 and 20. In some cases, the electroactive polymer 12 is incompressible, e.g. has a substantially constant volume under stress. In this case, the polymer 12 decreases in thickness as a result of the expansion in the planar directions 18 and 20. It should be noted that the present invention is not limited to incompressible polymers and deflection of the polymer 12 may not conform to such a simple relationship.

Application of a relatively large voltage difference between electrodes 14 and 16 on the transducer portion 10 shown in FIG. 2A will cause transducer portion 10 to change to a thinner, larger area shape as shown in FIG. 2B. In this manner, the transducer portion 10 converts electrical energy to mechanical energy. The transducer portion 10 may also be used to convert mechanical energy to electrical energy.

For actuation, the transducer portion 10 generally continues to deflect until mechanical forces balance the electrostatic forces driving the deflection. The mechanical forces include elastic restoring forces of the polymer 12 material, the compliance of electrodes 14 and 16, and any external resistance provided by a device and/or load coupled to the transducer portion 10, etc. The deflection of the transducer portion 10 as a result of an applied voltage may also depend on a number of other factors such as the polymer 12 dielectric constant and the size of polymer 12.

In one embodiment, electroactive polymer 12 is pre-strained. Pre-strain of a polymer may be described, in one or more directions, as the change in dimension in a direction after pre-straining relative to the dimension in that direction before pre-straining. The pre-strain may comprise elastic deformation of polymer 12 and be formed, for example, by stretching the polymer in tension and fixing one or more of the edges while stretched. For many polymers, pre-strain improves conversion between electrical and mechanical energy. The improved mechanical response enables greater mechanical work for an electroactive polymer, e.g., larger deflections and actuation pressures. In one embodiment, prestrain improves the dielectric strength of the polymer. In another embodiment, the pre-strain is elastic. After actuation, an elastically pre-strained polymer could, in principle, be unfixed and return to its original state. The pre-strain may be imposed at the boundaries using a rigid frame or may also be implemented locally for a portion of the polymer.

In one embodiment, pre-strain is applied uniformly over a portion of polymer 12 to produce an isotropic pre-strained polymer. By way of example, an acrylic elastomeric polymer may be stretched by 200 to 400 percent in both planar directions. In another embodiment, pre-strain is applied unequally in different directions for a portion of polymer 12 to produce an anisotropic pre-strained polymer. In this case, polymer 12 may deflect greater in one direction than another when actuated. While not wishing to be bound by theory, it is believed that pre-straining a polymer in one direction may increase the stiffness of the polymer in the pre-strain direction. Correspondingly, the polymer is relatively stiffer in the high pre-strain direction and more compliant in the low pre-strain direction and, upon actuation, more deflection occurs in the low pre-strain direction. In one embodiment, the deflection in direction 18 of transducer portion 10 can be enhanced by exploiting large pre-strain in the perpendicular direction 20. For example, an acrylic elastomeric polymer used as the transducer portion 10 may be stretched by 10 percent in direction 18 and by 500 percent in the perpendicular direction 20. The quantity of pre-strain for a polymer may be based on the polymer material and the desired performance of the polymer in an application. Pre-strain suitable for use with the present invention is further described in commonly owned, copending U.S. patent application Ser. No. 09/619,848, which is incorporated by reference for all purposes.

Generally, after the polymer is pre-strained, it may be fixed to one or more objects. Each object is preferably suitably stiff to maintain the level of pre-strain desired in the polymer. The polymer may be fixed to the one or more objects according to any conventional method known in the art such as a chemical adhesive, an adhesive layer or material, mechanical attachment, etc. Transducers and pre-strained polymers of the present invention are not limited to any particular geometry or type of deflection. For example, the polymer and electrodes may be formed into any geometry or shape including tubes and rolls, stretched polymers attached between multiple rigid structures, stretched polymers attached across a frame of any geometry—including curved or complex geometries, across a frame having one or more joints, etc. Deflection of a transducer according to the present invention includes linear expansion and compression in one or more directions, bending, axial deflection when the polymer is rolled, deflection out of a hole provided in a substrate, etc. Deflection of a transducer may be affected by how the polymer is constrained by a frame or rigid structures attached to the polymer. In one embodiment, a flexible material that is stiffer in elongation than the polymer is attached to one side of a transducer induces bending when the polymer is actuated.

Materials suitable for use as a pre-strained polymer with the present invention may include any substantially insulating polymer or rubber (or combination thereof) that deforms in response to an electrostatic force or whose deformation results in a change in electric field. One suitable material is NuSil CF19-2186 as provided by NuSil Technology of Carpenteria, Calif. Other exemplary materials suitable for use as a pre-strained polymer include silicone elastomers, acrylic elastomers such as VHB 4910 acrylic elastomer as produced by 3M Corporation of St. Paul, Minn., polyurethanes, thermoplastic elastomers, copolymers comprising PVDF, pressure-sensitive adhesives, fluoroelastomers, polymers comprising silicone and acrylic moieties, and the like. Polymers comprising silicone and acrylic moieties may include copolymers comprising silicone and acrylic moieties, polymer blends comprising a silicone elastomer and an acrylic elastomer, for example. Combinations of some of these materials may also be used as the electroactive polymer in transducers of this invention.

An electroactive polymer layer in transducers of the present invention may have a wide range of thicknesses. In one embodiment, polymer thickness may range between about 1 micrometer and 2 millimeters. Polymer thickness may be reduced by stretching the film in one or both planar directions. In many cases, electroactive polymers of the present invention may be fabricated and implemented as thin films. Thicknesses suitable for these thin films may be below 50 micrometers.

As electroactive polymers of the present invention may deflect at high strains, electrodes attached to the polymers should also deflect without compromising mechanical or electrical performance. Generally, electrodes suitable for use with the present invention may be of any shape and material provided that they are able to supply a suitable voltage to, or receive a suitable voltage from, an electroactive polymer. The voltage may be either constant or varying over time. In one embodiment, the electrodes adhere to a surface of the polymer. Electrodes adhering to the polymer are preferably compliant and conform to the changing shape of the polymer. Correspondingly, the present invention may include compliant electrodes that conform to the shape of an electroactive polymer to which they are attached. The electrodes may be only applied to a portion of an electroactive polymer and define an active area according to their geometry. Several examples of electrodes that only cover a portion of an electroactive polymer will be described in further detail below.

Various types of electrodes suitable for use with the present invention are described in commonly owned, copending U.S. patent application Ser. No. 09/619,848, which was previously incorporated by reference above. Electrodes described therein and suitable for use with the present invention include structured electrodes comprising metal traces and charge distribution layers, textured electrodes comprising varying out of plane dimensions, conductive greases such as carbon greases or silver greases, colloidal suspensions, high aspect ratio conductive materials such as carbon fibrils and carbon nanotubes, and mixtures of ionically conductive materials.

Materials used for electrodes of the present invention may vary. Suitable materials used in an electrode may include graphite, carbon black, colloidal suspensions, thin metals including silver and gold, silver filled and carbon filled gels and polymers, and ionically or electronically conductive polymers. In a specific embodiment, an electrode suitable for use with the present invention comprises 80 percent carbon grease and 20 percent carbon black in a silicone rubber binder such as Stockwell RTV60-CON as produced by Stockwell Rubber Co. Inc. of Philadelphia, Pa. The carbon grease is of the type such as NyoGel 756G as provided by Nye Lubricant Inc. of Fairhaven, Mass. The conductive grease may also be mixed with an elastomer, such as silicon elastomer RTV 118 as produced by General Electric of Waterford, N.Y., to provide a gel-like conductive grease.

It is understood that certain electrode materials may work well with particular polymers and may not work as well for others. By way of example, carbon fibrils work well with acrylic elastomer polymers while not as well with silicone polymers. For most transducers, desirable properties for the compliant electrode may include one or more of the following: low modulus of elasticity, low mechanical damping, low surface resistivity, uniform resistivity, chemical and environmental stability, chemical compatibility with the electroactive polymer, good adherence to the electroactive polymer, and the ability to form smooth surfaces. In some cases, a transducer of the present invention may implement two different types of electrodes, e.g. a different electrode type for each active area or different electrode types on opposing sides of a polymer.

Electrodes of the present invention may also include non-contacting electrodes. Non-contacting electrodes electrically communicate with an electroactive polymer using one or more electrodes that do not contact the polymer, and communicate typically through a medium. For example, the medium may include air, a vacuum, or a specialized gas that facilitates transfer of charge between the non-contacting electrode and the polymer. The charge may include positive or negative ions or electrodes that may be used for actuation, generation, sensing, or to diminish actuation applied to polymer in one or more specific polymer portions.

3. Multiple Active Areas

In some cases, electrodes cover a limited portion of an electroactive polymer relative to the total area of the polymer. This may be done to prevent electrical breakdown around the edge of a polymer or to achieve customized deflections for one or more portions of the polymer. As the term is used herein, an active area is defined as a portion of a transducer comprising polymer material and at least two electrodes. When the active area is used to convert electrical energy to mechanical energy, the active area includes a portion of polymer and electrodes having sufficient electrostatic force when a voltage is applied to enable deflection of the portion. When the active area is used to convert mechanical energy to electrical energy, the active area includes a portion of polymer and electrodes having sufficient deflection to enable a change in electrostatic energy. A polymer of the present invention may have multiple active areas.

In accordance with the present invention, the term "monolithic" is used herein to refer to electroactive polymers and transducers comprising a plurality of active areas on a single polymer. FIG. 3A illustrates a monolithic transducer 150 comprising a plurality of active areas on a single polymer 151 in accordance with one embodiment of the present invention. The monolithic transducer 150 converts between electrical energy and mechanical energy. The monolithic transducer 150 comprises an electroactive polymer 151 having two active areas 152a and 152b. Polymer 151 may be held in place using, for example, a rigid frame (not shown) attached at the edges of the polymer. Coupled to active areas 152a and 152b are wires 153 that allow electrical communication between active areas 152a and 152b and allow electrical communication with communication electronics 155.

Active area 152a has top and bottom electrodes 154a and 154b that are attached to polymer 151 on its top and bottom surfaces 151c and 151d, respectively. Electrodes 154a and 154b provide or receive electrical energy across a portion 151a of the polymer 151. Portion 151a may deflect with a change in electric field provided by the electrodes 154a and 154b. For actuation, portion 151a comprises the polymer 151 between the electrodes 154a and 154b and any other portions of the polymer 151 having sufficient electrostatic force to enable deflection upon application of voltages using the electrodes 154a and 154b. When active area 152a is used as a generator to convert from electrical energy to mechanical energy, deflection of the portion 151a causes a change in electric field in the portion 151a that is received as a change in voltage difference by the electrodes 154a and 154b.

Active area 152b has top and bottom electrodes 156a and 156b that are attached to the polymer 151 on its top and bottom surfaces 151c and 151d, respectively. Electrodes 15a and 156b provide or receive electrical energy across a portion 151b of the polymer 151. Portion 151b may deflect with a change in electric field provided by the electrodes 156a and 156b. For actuation, portion 151b comprises the polymer 151 between the electrodes 156a and 156b and any other portions of the polymer 151 having sufficient stress induced by the electrostatic force to enable deflection upon application of voltages using the electrodes 156a and 156b. When active area 152b is used as a generator to convert from electrical energy to mechanical energy, deflection of the portion 151b causes a change in electric field in the portion 151b that is received as a change in voltage difference by the electrodes 156a and 156b. Further examples and description of monolithic electroactive transducers and systems is provided in commonly-owned, copending U.S. patent application Ser. No. 09/779,203, which is incorporated herein be reference for all purposes.

Master/slave functionality for monolithic transducer 150 may be flexibly configured. For example, one active area of monolithic transducer 150 may be configured to act as a master of the master/slave electroactive polymer system and the other active area disposed on the monolithic polymer may be configured to act as the slave. In this case, the master receives mechanical deflection from an external source and produces an electrical energy change. Communication electronics 155 are configured to provide at least a portion of the resulting electrical energy change to the slave. In another embodiment for monolithic electroactive polymer master/slave systems, a portion of one monolithic electroactive polymer is coupled to a portion of another monolithic electroactive polymer. With suitable control and communication electronics, any active area of either electroactive polymer may act as a master or slave.

Each of the electrode pairs 154 and 156 are arranged such that they provide independent electrical communication with each of the active areas 152a and 152b. Independence of the electrodes 154 and 156 allows electrical energy to be separately supplied to (or removed from) the electrodes 154 and 156; thus allowing independent control and separate actuation for each of the active areas 152a and 152b.

The active areas for monolithic polymers and transducers of the present invention may be flexibly arranged. In some cases, polymer material outside an active area may act as an external spring force on the active area during deflection. More specifically, polymer material outside the active area may resist active area deflection by its contraction or expansion. Removal of the voltage difference and the induced charge causes the reverse effects. In one embodiment, active areas in a polymer are arranged such that the elasticity of the active areas is balanced. In another embodiment, a transducer of the present invention comprises a plurality of symmetrically arranged active areas.

Figure 3B:
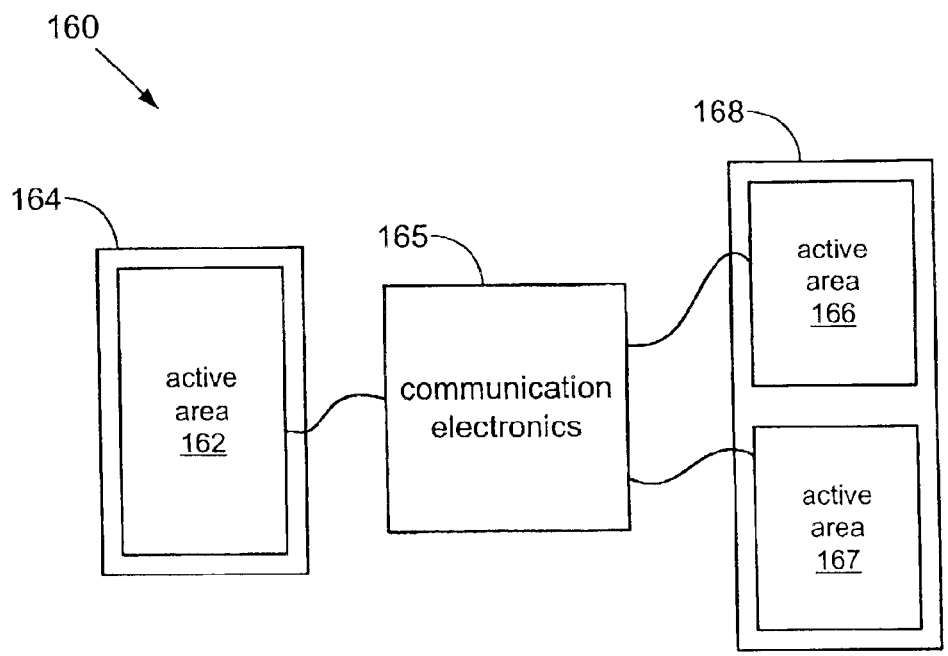
FIG. 3B illustrates a master/slave system comprising a plurality of active areas on multiple polymers in accordance with another embodiment of the present invention.

FIG. 3B illustrates an exemplary master/slave system 160 comprising a plurality of active areas on multiple polymers in accordance with another embodiment of the present invention. Master/slave system 160 comprises active area 162 included on electroactive polymer 164, communication electronics 165, and active areas 166 and 167 included on monolithic polymer 168. Active area 162 is larger than either of active areas 166 and 167.

Communication electronics 165 receive and provide electrical communication in system 160. This may include temporal and quantitative control and distribution of electrical energy generated by one of the active areas. For electrical energy received from active area 162 for example, communication electronics 165 may provide (i) all of the electrical energy to active area 166, or (ii) all of the electrical energy to active area 167, or (iii) portions of the electrical energy may be distributed between active areas 166 and 167. Conversely, communication electronics 165 may combine electrical energy generated from multiple active areas. For example, active areas 166 and 167 may be used to generate electrical energy that communication electronics 165 combine and provide to active area 162. The electrical energy combined in this manner may include energy that is received at different times and via different voltage levels.

Electrical energy generated by an active area of the present invention may be derived from mechanical energy provided by a wide variety of external sources. In general, the sources deflect the active area. One example includes mechanical energy provided by a person, such as when the person's footwear contacts a surface during human bipedal motion or hand movements that power electroactive polymer transducers included in a glove that a person wears.

Figure 3C:
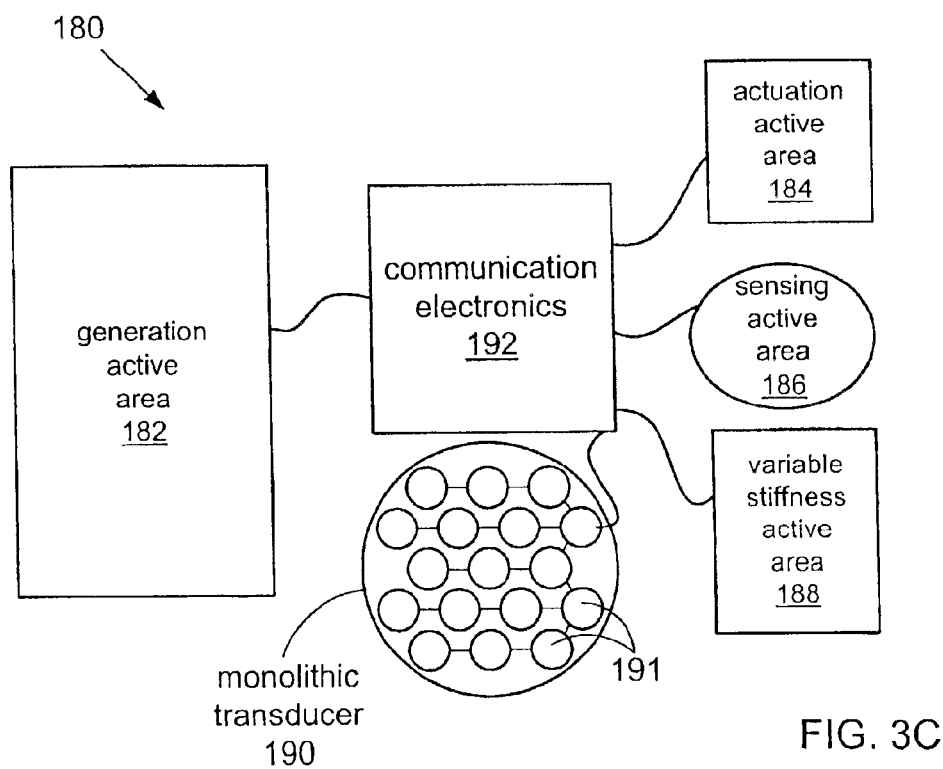
FIG. 3C illustrates a master/slave system comprising a plurality of active areas on multiple polymers in accordance with another embodiment of the present invention.

FIG. 3C illustrates an exemplary master/slave system 180 comprising a plurality of active areas on multiple polymers in accordance with another embodiment of the present invention. The active areas in system 180 are each dedicated to a specific set of functions. Master/slave system 180 includes generation active area 182, actuation active area 184, sensing active area 186, variable stiffness active area 188, and combined generation and variable stiffness monolithic transducer 190. Combined function monolithic transducer 190 includes a number of circular diaphragm active areas 191 disposed on an electroactive polymer. Communication electronics 192 provide electrical communication between each of the active areas in system 180.

Generation active area 182 provides at least some of the power for system 180. This energy is received by communication electronics 192 and provided, as desired in quantity and time, to one or more of the other active areas. In some cases, active areas 191 from polymer 190 may also generate electrical energy for system 180. For example, active area 182 may be disposed in a top portion of footwear to receive mechanical energy produced in this region during human bipedal locomotion. Active area 182 then converts this mechanical energy to electrical energy, which is received by communication electronics 192. In addition, monolithic polymer 190 may be disposed in the heel of a shoe to generate electrical energy from mechanical energy obtained when a person's foot contacts the ground during bipedal human locomotion. Communication electronics 192 provide the electrical energy generated by active area 182 and transducer 190 to other active areas. In the shoe example, actuation active area 184 may use the electrical energy to tighten the shoe. Variable stiffness active area 188 may be included in a transducer disposed around the ankle of a person and use electrical energy provided by communication electronics 192 to vary the stiffness provided by the shoe in the ankle region. Sensing active area 186 may be included in a sensor that detects a property of the human bipedal locomotion, such as the amount of force generated in each step. When disposed in the heel portion of a shoe, combined function transducer 190 may also use electrical energy provided by communication electronics 192 to vary the stiffness of the heel. In addition, system 180 may also comprise a battery or other suitable electrical storage device in electrical communication with communication electronics 192 that temporarily stores electrical energy generated by active area 182 or transducer 190 and/or provides electrical energy to one of the active areas.

Aside from the exemplary master/slave devices and systems shown and described herein, other active area configurations are possible and the present invention is not meant to be limited by the specific examples shown herein.

Figure 8:
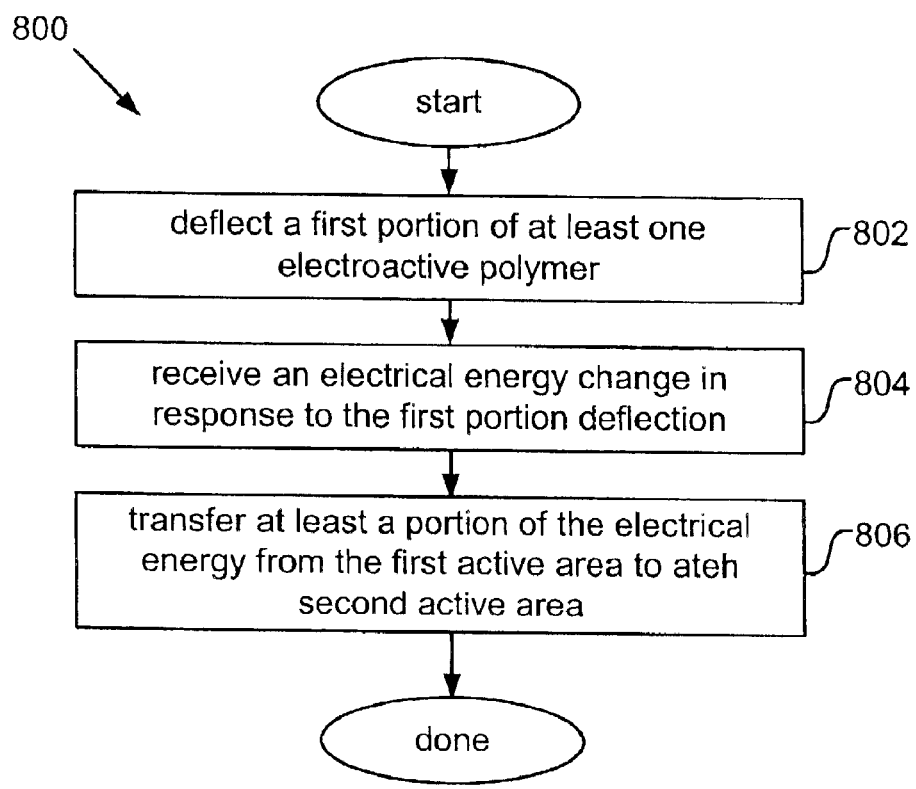
FIG. 8 illustrates a process flow for using multiple electroactive polymer active areas in accordance with one embodiment of the present invention.

FIG. 8 illustrates a process flow 800 for using multiple electroactive polymer active areas in accordance with one embodiment of the present invention. Process flow 800 relies on at least one electroactive polymer and at least two active areas—designated here as first and second active areas. Methods in accordance with the present invention may include up to several additional steps not described or illustrated here in order not to obscure the present invention.

Process flow 800 typically begins with deflecting a first portion of at least one electroactive polymer (802). The portion may be included in the first active area or may be another portion of the polymer associated with a mechanical coupling, for example. An electrical energy change is received in response to the first portion deflection via the electrodes for the first active area (804). For generation and production of electrical energy, an electric field is first provided electrically to the first active area before the deflection. The change in electric field is less than the electric field needed to actuate the first portion to its existing configuration. The deflection then increases or decreases the electrical field and electrical energy between the first active area electrodes.

At least a portion of the electrical energy change from the first portion deflection is transferred from the first active area to the second active area (806). Typically, this comprises communicating the electrical energy change from a first active area electrode in electrical communication with the first active area to a second active area electrode in electrical communication with a second active area. The rate of electrical energy change transferred from the first active area electrodes to the second active area electrodes may be regulated, e.g., delayed, amplified, or divided as desired. In some cases, some electrical energy generated by the first active area is stored in a battery or capacitor. Depending on the amount of electrical energy transferred to the second active area, the size of the second active area, and the presence of any external loading, the second active area may deflect in response to the change in electric field provided to the first portion. In other cases, electrical energy may be used to increase the stiffness of the second portion.

4. Communication Electronics

Communication electronics are disposed between the master and slave to provide electrical communication therebetween. Typically, the communication electronics provide electrical communication between electrodes included in the master portion of the master/slave system and electrodes included in the slave portion of the master/slave system.

The communication electronics may be configured to provide a wide variety of relationships between the master and slave. In general, the communication electronics transfer the changes in electrical energy or state of the master to the slave. Often, this includes receiving electrical energy generated by the master in response to external deflection and transferring at least a portion of the energy to the slave. The communication electronics may include various regulation functions for transferring the electrical energy between the master and slave. Regulation may include temporal (e.g., time delays) and quantitative (amplification, biasing, energy division among multiple slaves, energy storage, etc.) changes, for example.

The communication electronics may be passive. In one embodiment, passive communication electronics refers to communication electronics that react without logic or active control. In another embodiment, passive means external energy is not supplied to do the desired work. The use of a small amount of energy to power the logic elements is incidental. Typically, these passive communication electronics automatically or naturally respond in a substantially consistent manner. Passive communication electronics disposed between a master and slave may include a wire, diode, resistor, inductor, capacitor, or a system comprising multiples and combinations of these elements. Passive electrical communication between a master and slave allows systems of the present invention to be implemented with minimal control, or respond passively without any control.

In a specific embodiment, the passive communication electronics simply comprise an open electrical wire. The open wire allows electrical energy changes in the master to directly and immediately affect the slave. For example, the open wire allows electrical energy generated by the master to immediately flow to the slave. Thus, when the master is deflected and produces electrical energy, the electrical state of the slave responds only after a delay corresponding to the electrical propagation of current through the wire between the master and slave (almost immediate). When the master deflects back to its original position, or a position corresponding to lower electrical energy, or its electrical state otherwise changes, the slave responds almost immediately. Open wires between active areas allow passive and immediate response in any direction. Thus, for systems where two (or more) active areas may each act as either a master or slave relative to one another, an open wire allows direct and immediate electrical energy change propagation from one active area to the other, regardless of which one is currently the master.

The communication electronics may also introduce various time response relationships between a master and slave. For example, a high resistance resistor may be included in the communication electronics between a master and slave to regulate the rate of charge flow therebetween. As the resistance of the resistor increases, the rate of current flow between master and slave decreases. Again, the resistor provides this functionality for either direction of current flow between two active areas.

A diode may employed in the communication electronics to provide directional control. In the forward diode direction (as determined by the diode orientation), the diode allows current to flow substantially unimpeded and functions in the manner as described above with respect to a wire. In the opposite direction, the diode prevents the flow of current from slave back to the master. In this manner, the diode creates a one directional master/slave relationship between two active areas.

Diodes may also provide ratcheting effects between a master and slave. In this case, when the master is deflected and produces electrical energy, the slave responds (e.g., deflects or increases in stiffness) to the electrical energy provided through the diode. However, when the master deflects back to its original position, or a position corresponding to lower electrical energy, the slave holds its electrical state or deflection corresponding to the electrical state. If the master is connect to a low voltage power supply via a second diode or uses another manner to resupply its initial charge at each cycle, this process may be repeated to provide a pumping effect in which the master is repeatedly deflected to produce a relatively small electrical energy change in order to produce a time integrated and relatively large response of the slave. The mechanical energy input to the master is used to increase the electrical energy (higher voltage for each unit of charge) to the slave (e.g. beyond what the power supply can provide). Here, electrical energy is generated in small increments by the master and each small increments is accumulated in the slave using the one-way electrical flow provided by the diode. An electrical discharge may be included in electrical communication with the slave to release electrical energy accumulated in this manner as desired.

To achieve another time response relationship, one or more and inductors may be used to introduce a time delay before transferring electrical energy from a master to a slave. Typically, the inductor delays slave response relative to the deflection rate of the master. If the master is deflected at a high speed, an inductor may then be employed to delay slave response. This may be beneficial for example, when differences in timing are desired between the master input and the slave response. In some cases, the inductor influences timing, but not necessarily the deflection rate.

Alternatively, one or more capacitors may be used in the communication electronics. The capacitor is suitable for de-amplification of the electrical energy provided by the master. Consider, for example, that an infinite or extremely large capacitance is connected in parallel with the slave unit. Since the capacitance is infinite or extremely large, when the master adds or removes charge from the slave-capacitor combination, the voltage the slave experiences is substantially unchanged and therefore its deflection will be zero or negligible. On the other hand, if the capacitance is zero the voltage on the slave will change according to its capacitance and how much charge it receives. If the charge is enough to appreciably change the slave's voltage between electrodes in the active area, it can deflect an appreciable amount as a result. Thus, by suitable choice of the capacitor size in the communication electronics, the response of the slave can be adjusted from full response to zero response.

Combinations of these elements may be implemented for various relationships between a master and slave. For example, the pumping action provided by a diode may be combined with an inductor to generate a large and delayed response from a slave that is powered by a motor being deflected at high frequencies. One or more capacitors and resistors may be combined to provide master/slave systems having various passive time adaptive properties. The time adaptive properties may then be tuned according to an application. In addition, active transistor elements may also be incorporated into the communication electronics The transistors may be triggered to a conducting state by the master. For example, motion of the master may close a mechanical limit switch at either end of its stroke to trigger a transistor and close the connection between master and slave. The slave will then have a sharp response even though the master moves more slowly. Breakover diodes (passive elements), which conduct when the voltage across them exceeds a certain value, may also be used for this purpose. Active elements such as voltage amplifiers can be used to enhance the power provided by the master, and active computer or control elements controlling switches such as transistors can be used to provide complex responses by the slave based on criterion input by the master or using the master input plus external sensing inputs.

In addition to passive systems described above, active systems relying on logic and switches may be implemented in master/slave electroactive polymer systems. The logic may correspond to one more processors such as microprocessors implemented in the communication electronics. The logic controls electrical components within the communications electronics. Electrical components controlled by the logic may include one or more passive elements as described above, or one or more switches dedicated to a particular electrical communication pathway. In the former case for example, a variable resistor (or its electrical equivalent using transistor circuits) may be controlled by the logic device. In the latter case for example, two electrical pathways may be disposed between two active areas, where each pathway includes a diode and switch. In this case, the diodes restrict flow between the active areas in opposite directions and the switches allow current flow to be controlled for either direction—as determined by the logic device.

In another embodiment, an electrical storage device is included in the communication electronics and configured to store electrical energy produced by the master. The electrical storage device may then provide the electrical energy to the slave in a controlled manner. For example, one or more batteries, or one or more capacitors, may temporarily store electrical energy generated by the master. Logic may then be implemented to affect both the collection of electrical energy from the master and the provision of electrical energy to the slave according to a desired output response of the slave.

Figure 4:
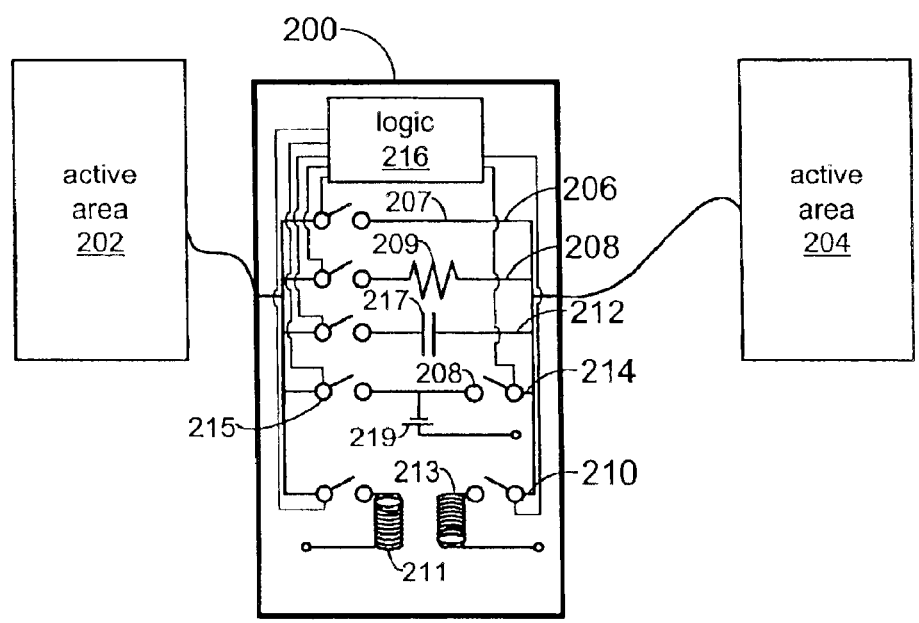
FIG. 4 illustrates communication electronics between two active areas and in accordance with one embodiment of the present invention.

FIG. 4 illustrates exemplary communication electronics 200 between two active areas 202 and 204 in accordance with a specific embodiment of the present invention. Communication electronics 200 include five electrical pathways 206, 208, 210, 212, and 214. Each pathway 206, 208, 210, 212, and 214 includes its own dedicated on/off 215 switch controlled by logic device 216. Pathway 206 includes an open wire 207 that allows free electrical communication between active areas 202 and 204. Pathway 208 comprises a resistor 209 that regulates charge flow between active areas 202 and 204. Pathway 208 also allows dissipative losses for electrical energy produced by one of the active areas (damping). Pathway 212 comprises a capacitor 217 that de-amplifies electrical energy between active areas 202 and 204. Pathway 214 comprises a battery 219 that is charged by electrical energy generated by either active area 202 or 204. Pathway 210 includes inductive coupling using inductors 211 and 213 disposed between active areas 202 and 204. Logic 216 controls the switch 215 for each pathway and the electrical communication between active areas 202 and 204.

The input mechanical energy may vary over a significant range of frequencies. In many applications such as receiving human mechanical energy, the types of motions used to deflect the master tend to be large motions with low cycling frequencies. An advantage of the master/slave systems of the present invention is that master/slave active areas may be tuned to efficiently alter energy generated by large motions with low cycling frequencies. By contrast, electromagnetic generators and motors usually require transmissions such as complex gearing systems to efficiently work at low frequencies. Given that communication electronics as described above may accommodate for differences in the master deflection frequency and a desired output frequency for slave mechanical response (e.g., deflection or changing the stiffness), the present invention allows master/slave systems of the present invention to provide any desired time relationship between the master and slave—despite a wide variety of mechanical input frequency to the master and desired output frequencies for the slave.

5. Multifunctionality

Electroactive polymers have many functional uses. In addition to actuation, active areas of the present invention may also be used for generation and production of electrical energy, sensing, and variable stiffness or damping in a wide variety of applications.

FIGS. 2A and 2B may be used to show one manner in which the transducer portion 10 converts mechanical energy to electrical energy. For example, if the transducer portion 10 is mechanically stretched by external forces to a thinner, larger area shape such as that shown in FIG. 2B, and a relatively small voltage difference (less than that necessary to actuate the film to the configuration in FIG. 2B) is applied between electrodes 14 and 16, the transducer portion 10 will contract in area between the electrodes to a shape such as in FIG. 2A when the external forces are removed. Stretching the transducer refers to deflecting the transducer from its original resting position—typically to result in a larger net area between the electrodes, e.g. in the plane defined by directions 18 and 20 between the electrodes. The resting position refers to the position of the transducer portion 10 having no external electrical or mechanical input and may comprise any pre-strain in the polymer. Once the transducer portion 10 is stretched, the relatively small voltage difference is provided such that the resulting electrostatic forces are insufficient to balance the elastic restoring forces of the stretch. The transducer portion 10 therefore contracts, and it becomes thicker and has a smaller planar area in the plane defined by directions 18 and 20 (orthogonal to the thickness between electrodes). When polymer 12 becomes thicker, it separates electrodes 14 and 16 and their corresponding unlike charges, thus raising the electrical energy and voltage of the charge. Further, when electrodes 14 and 16 contract to a smaller area, like charges within each electrode compress, also raising the electrical energy and voltage of the charge. Thus, with different charges on electrodes 14 and 16, contraction from a shape such as that shown in FIG. 2B to one such as that shown in FIG. 2A raises the electrical energy of the charge. That is, mechanical deflection is being turned into electrical energy and the transducer portion 10 is acting as a 'generator'.

When a relatively small voltage difference is applied between electrodes 14 and 16, deflection of transducer portion 10 will tend to change the voltage difference between the electrodes or drive charge to or from the electrodes, or do both, depending on the electrical state imposed on the electrodes 14 and 16. As polymer 12 changes in size, the changing electrical properties and voltage may be detected, dissipated, and/or used. For example, the change in voltage difference between the electrodes may be used to drive current to or from one of the electrodes which is dissipated through a resistor.

Some or all of the charge and energy can be removed when the transducer portion 10 is fully contracted in the plane defined by directions 18 and 20. Alternatively, some or all of the charge and energy can be removed during contraction. If the electric field pressure in the polymer increases and reaches balance with the mechanical elastic restoring forces and external load during contraction, the contraction will stop before full contraction, and no further elastic mechanical energy will be converted to electrical energy. Removing some of the charge and stored electrical energy reduces the electrical field pressure, thereby allowing contraction to continue. The exact electrical behavior of the transducer portion 10 when operating in generator mode depends on any electrical and mechanical loading as well as the intrinsic properties of polymer 12 and electrodes 14 and 16.

In some cases, the transducer portion 10 may be described electrically as a variable capacitor. The capacitance decreases for the shape change going from that shown in FIG. 2B to that shown in FIG. 2A. Typically, the voltage difference between electrodes 14 and 16 will be raised by contraction. This is normally the case, for example, if additional charge is not added or subtracted from electrodes 14 and 16 during the contraction process. The increase in electrical energy, U, may be illustrated by the formula $U=0.5\, Q^2/C$, where Q is the amount of positive charge on the positive electrode and C is the variable capacitance which relates to the intrinsic dielectric properties of polymer 12 and its geometry. If Q is fixed and C decreases, then the electrical energy U increases. The increase in electrical energy and voltage can be recovered or used in a suitable device or electronic circuit in electrical communication with electrodes 14 and 16. In addition, the transducer portion 10 may be mechanically coupled to a mechanical input that deflects the polymer and provides mechanical energy.

For a transducer having a substantially constant thickness, one mechanism for differentiating the performance of the transducer, or a portion of the transducer associated with a single active area, as being an actuator or a generator is in the change in net area orthogonal to the thickness associated with the polymer deflection. For these transducers or active areas, when the deflection causes the net area of the transducer/active area to decrease and there is charge on the electrodes, the transducer/active area is converting from mechanical to electrical energy and acting as a generator. Conversely, when the deflection causes the net area of the transducer/active area to increase and charge is on the electrodes, the transducer/active area is converting electrical to mechanical energy and acting as an actuator. The change in area in both cases corresponds to a reverse change in film thickness, i.e. the thickness contracts when the planar area expands, and the thickness expands when the planar area contracts. Both the change in area and change in thickness determine the amount of energy that is converted between electrical and mechanical. Since the effects due to a change in area and corresponding change in thickness are complementary, only the change in area will be discussed herein for sake of brevity. In addition, although deflection of an electroactive polymer will primarily be discussed as a net increase in area of the polymer when the polymer is being used in an actuator to produce mechanical energy, it is understood that in some cases (i.e. depending on the loading), the net area may decrease to produce mechanical work. Thus, devices of the present invention may include both actuator and generator modes, depending on how the polymer is arranged and applied.

Electroactive polymers of the present invention may also be configured as a sensor. Generally, electroactive polymer sensors of this invention detect a "parameter" and/or changes in the parameter. The parameter is usually a physical property of an object such as its temperature, density, strain, deformation, velocity, location, contact, acceleration, vibration, volume, pressure, mass, opacity, concentration, chemical state, conductivity, magnetization, dielectric constant, size, etc. In some cases, the parameter being sensed is associated with a physical "event". The physical event that is detected may be the attainment of a particular value or state of a physical or chemical property.

An electroactive polymer sensor is configured such that a portion of the electroactive polymer deflects in response to the change in a parameter being sensed. The electrical energy state and deflection state of the polymer are related. The change in electrical energy or a change in the electrical impedance of an active area resulting from the deflection may then be detected by sensing electronics in electrical communication with the active area electrodes. This change may comprise a capacitance change of the polymer, a resistance change of the polymer, and/or resistance change of the electrodes, or a combination thereof. Electronic circuits in electrical communication with electrodes detect the electrical property change. If a change in capacitance or resistance of the transducer is being measured for example, one applies electrical energy to electrodes included in the transducer and observes a change in the electrical parameters.

In one embodiment, deflection is input into an active area sensor in some manner via one or more coupling mechanism. In one embodiment, the changing property or parameter being measured by the sensor corresponds to a changing property of the electroactive polymer, e.g. displacement or size changes in the polymer, and no coupling mechanism is used. Sensing electronics in electrical communication with the electrodes detect change output by the active area. In some cases, a logic device in electrical communication with sensing electronics of sensor quantifies the electrical change to provide a digital or other measure of the changing parameter being sensed. For example, the logic device may be a single chip computer or microprocessor that processes information produced by sensing electronics. Electroactive polymer sensors are further described in Ser. No. 10/007,705, which is incorporated herein by reference for all purposes.

An active area may be configured such that sensing is performed simultaneously with actuation of the active area. For a monolithic transducer, one active area may be responsible for actuation and another for sensing. Alternatively, the same active area of a polymer may be responsible for actuation and sensing. In this case, a low amplitude, high frequency AC (sensing) signal may be superimposed on the driving (actuation) signal. For example, a 1000 Hz sensing signal may be superimposed on a 10 Hz actuation signal. The driving signal will depend on the application, or how fast the actuator is moving, but driving signals in the range from less than 0.1 Hz to about 1 million Hz are suitable for many applications. In one embodiment, the sensing signal is at least about 10 times faster than the motion being measured. Sensing electronics may then detect and measure the high frequency response of the polymer to allow sensor performance that does not interfere with polymer actuation. Similarly, if impedance changes are detected and measured while the electroactive polymer transducer is being used as a generator, a small, high-frequency AC signal may be superimposed on the lower-frequency generation voltage signal. Filtering techniques may then separate the measurement and power signals.

Slave active areas of the present invention may also be configured to provide variable stiffness and damping functions. In one embodiment, open loop techniques are used to control stiffness and/or damping of a device employing an electroactive polymer transducer; thereby providing simple designs that deliver a desired stiffness and/or damping performance without sensor feedback. For example, control electronics in electrical communication with electrodes of the transducer supply a substantially constant charge to the electrodes. Alternately, the control electronics supply a substantially constant voltage to the electrodes. In either case, conditioning electronics modulate energy produced by a master to the desired electrical state imposed on the slave to achieve the desired stiffness and/or damping. Systems employing an electroactive polymer transducer offer several techniques for providing stiffness and/or damping control.

6. Conditioning Electronics

In addition to communication electronics disposed between active areas, devices and systems of the present invention may also rely on conditioning electronics that provide or receive electrical energy from electrodes of an active area for one of the electroactive polymer functions mentioned above. Conditioning electronics in electrical communication with one or more active areas may include functions such as stiffness control, energy dissipation, electrical energy generation, polymer actuation, polymer deflection sensing, control logic, etc.

For actuation, electronic drivers may be connected to the electrodes. The voltage provided to electrodes of an active area will depend upon specifics of an application. In one embodiment, an active area of the present invention is driven electrically by modulating an applied voltage about a DC bias voltage. Modulation about a bias voltage allows for improved sensitivity and linearity of the transducer to the applied voltage. For example, a transducer used in an audio application may be driven by a signal of up to 200 to 100 volts peak to peak on top of a bias voltage ranging from about 750 to 2000 volts DC.

Suitable actuation voltages for electroactive polymers, or portions thereof, may vary based on the material properties of the electroactive polymer, such as the dielectric constant, as well as the dimensions of the polymer, such as the thickness of the polymer film For example, actuation electric fields used to actuate polymer 12 in FIG. 2A may range in magnitude from about 0 V/m to about 440 MV/m. Actuation electric fields in this range may produce a pressure in the range of about 0 Pa to about 10 MPa. In order for the transducer to produce greater forces, the thickness of the polymer layer may be increased. Actuation voltages for a particular polymer may be reduced by using other polymers with a higher dielectric constant or lower modulus of elasticity, or by decreasing the polymer thickness, for example.

For a master, mechanical energy may be applied to the active area in a manner that allows electrical energy changes to be removed from the active area. Many methods for applying mechanical energy and removing an electrical energy change from the active area are possible. Master/slave systems may be designed that utilize one or more of these methods to receive an electrical energy change and provide the energy change to the slave. For generation and sensing, the generation and utilization of electrical energy from the master may require conditioning electronics of some type. For instance, at the very least, a minimum amount of circuitry is needed to remove electrical energy from the active area. Further, as another example, circuitry of varying degrees of complexity may be used to increase the efficiency or quantity of electrical generation in a particular active area or to convert an output voltage to a more useful value.

Figure 5A:
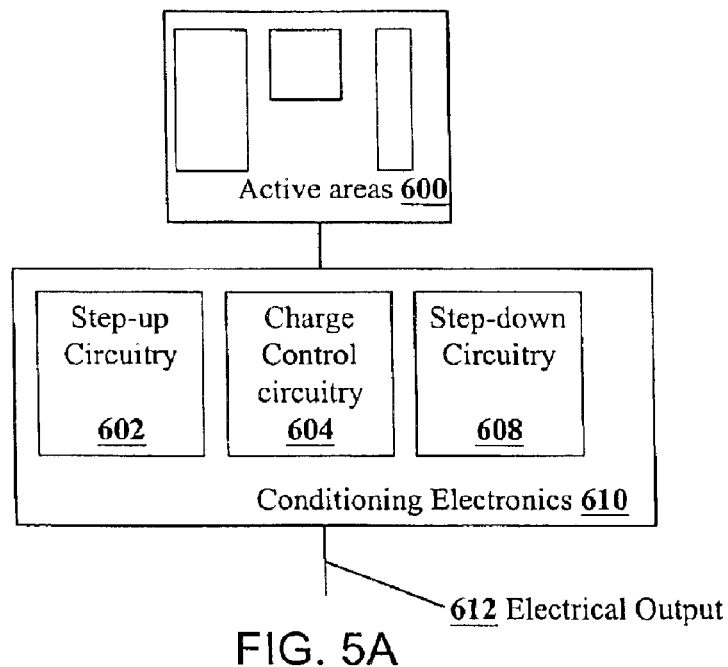
FIG. 5A is block diagram of active areas in electrical communication with conditioning electronics.

FIG. 5A is block diagram of one or more active areas 600 connected to power conditioning electronics 610. Potential functions that may be performed by the power conditioning electronics 610 include but are not limited to 1) voltage step-up performed by step-up circuitry 602, which may be used when applying a voltage to active areas 600, 2) charge control performed by the charge control circuitry 604 which may be used to add or to remove charge from the active areas 600 at certain times, 3) voltage step-down performed by the step-down circuitry 608 which may be used to adjust an electrical output voltage to a slave. All of these functions may not be required in the conditioning electronics 610. For instance, some master devices may not use step-up circuitry 602, other master devices may not use step-down circuitry 608, or some master devices may not use step-up circuitry and step-down circuitry. Also, some of the circuit functions may be integrated. For instance, one integrated circuit may perform the functions of both the step-up circuitry 602 and the charge control circuitry 608.

Figure 5B:
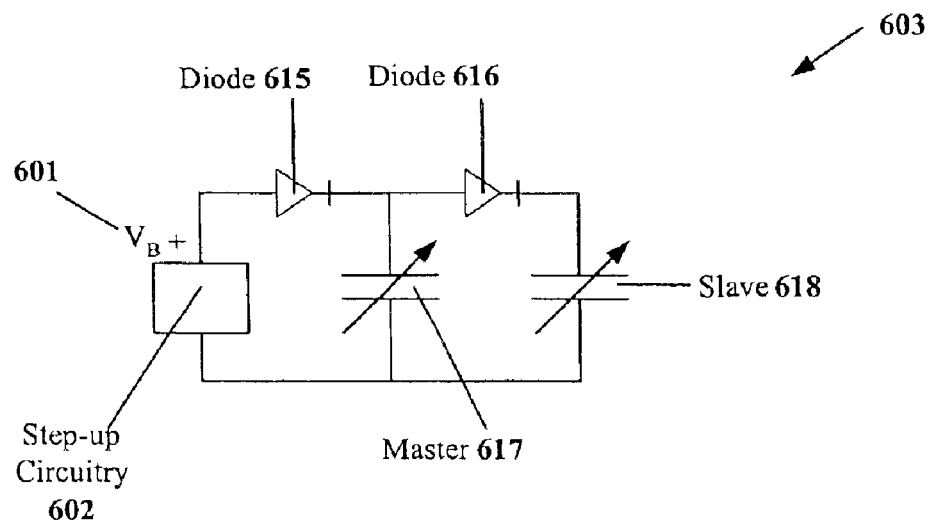
FIG. 5B is a circuit schematic of a master/slave system for one embodiment of the present invention.

FIG. 5B is a circuit schematic of a master/slave system 603 employing active areas 617 and 618 for one embodiment of the present invention. As described above, transducers of the present invention may behave electrically as variable capacitors. To understand the operation of the master/slave system 603, operational parameters of the master/slave system 603 at two times, $t_1$ and $t_2$ may be compared. Without wishing to be constrained by any particular theory, a number of theoretical relationships regarding the electrical performance the master/slave system 603 are developed. These relationships are not meant in any manner to limit the manner in which the described devices are operated and are provided for illustrative purposes only.

At a first time, $t_1$, the master 617 may possess a capacitance, $C_1$, and the voltage across the master 617 may be voltage 601, $V_B$. The voltage 601, $V_B$, may be provided by the step-up circuitry 602. At a second time $t_2$, later than time $t_1$, the master 617 may posses a capacitance $C_2$ which is lower than the capacitance $C_1$. Generally speaking, the higher capacitance C1 occurs when the polymer master 617 is stretched in area, and the lower capacitance C2 occurs when the polymer master 617 is contracted or relaxed in area. Without wishing to bound by a particular theory, the change in capacitance of a polymer with electrodes may be estimated by well known formulas relating the capacitance to the film's area, thickness, and dielectric constant.

The decrease in capacitance of the master 617 between $t_1$ and $t_2$ will increase the voltage across the master 617. The increased voltage may be used to drive current through diode 616. The diode 615 may be used to prevent charge from flowing back into the step-up circuitry at such time. The two diodes, 615 and 616, function as charge control circuitry 604 for master/slave system which is part of the power conditioning electronics 610 (see FIG. 5A). The current passed through diode 616 is passed to slave 618, which uses the electrical energy to produce mechanical energy. If the master 617 is repeatedly mechanically stretched and contracted, charge is pumped to slave 618 until its voltage reaches a maximum. The maximum voltage on slave 618 is determined by the input bias voltage $V_B$, the change in capacitance of the master as it is stretched and contracted, and by the leakage currents. More complex charge control circuits may be developed depending on the configuration of the system 603 and are not limited to the design in FIG. 5B. Other suitable electroactive polymer generator circuits are further described in commonly-owned copending U.S. patent application Ser. No. 09/792,877, which is incorporated herein by reference for all purposes.

A slave active may also area provide stiffness and/or damping onto a mechanical system. In one embodiment, the slave stiffness and/or damping is controlled using open loop techniques. As the terms used herein, open loop refers to systems designed or configured such that a desired stiffness and/or damping is input directly into the control elements unaffected by the output performance of the system. Open loop techniques as described herein advantageously allow master/slave systems as described herein to react passively to provide a desired performance. To damp vibrations then, the system does not require a sensor. In one application, the resonant frequency of a mechanical system is influenced by the stiffness provided by an active area controlled by an open loop electrical circuit.

By adjusting the electrical state provided to a slave, mechanical properties such as the stiffness of the slave active area may be varied and controlled. Thus, a system for providing variable stiffness typically comprises control electronics in electrical communication with electrodes included in the slave. The control electronics are designed or configured to set or change an electrical state or electrical impedance that results in the desired stiffness for the slave or associated device. The electrical state or electrical impedance typically relates to temporal electrical conditions applied by the control electronics to the slave, via the electrodes, to obtain the desired force per unit length deflection, or the desired damping, of the slave—or an associated mechanical interface.

Figure 5C:
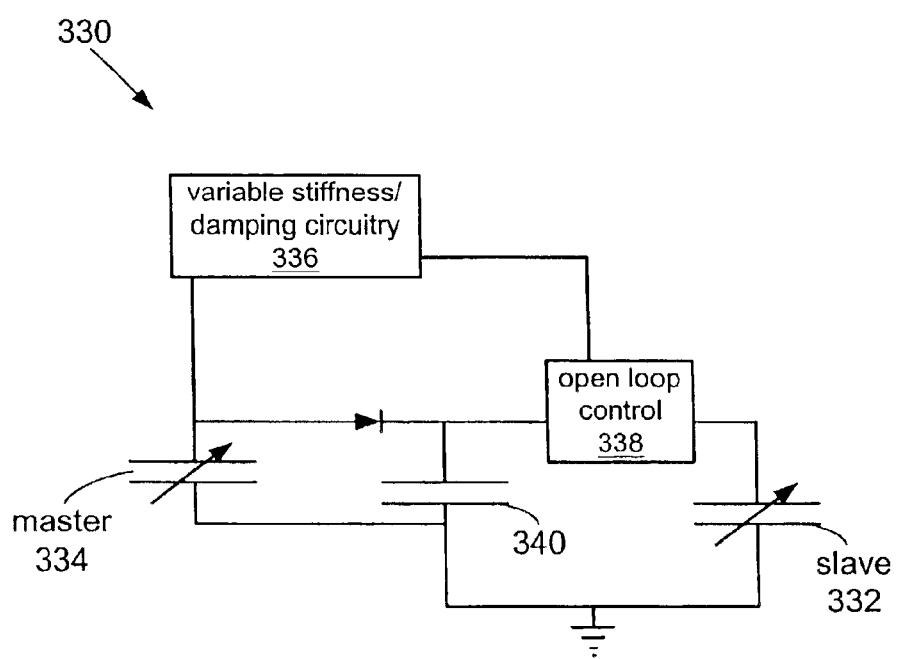
FIG. 5C illustrates an electrical schematic of an open loop variable stiffness/damping system in accordance with one embodiment of the present invention.

FIG. 5C illustrates an electrical schematic of an open loop variable stiffness/damping master/slave system 330 in accordance with one embodiment of the present invention. While system 330 will now be described as an apparatus composed of units, those skilled in the area will recognize that the present invention encompasses a method, process or control software having as steps the actions performed by each unit and described below. System 330 comprises an slave active area 332, master active area 334, control electronics comprising variable stiffness/damping circuitry 336 and open loop control 338, and buffer capacitor 340.

Master active area 334 acts as a generator and provides electrical energy used in system 330. Master 334 is initially supplied by charge and energy using a power supply which may employ step up circuitry such as that indicated in FIG. 5B. In this case, master active area 334 sets the minimum voltage for slave active area 332. Adjusting this minimum voltage, together with open loop control 338, adjusts the stiffness provided by slave active area 332. Master active area 334 also supplies charge to system 330. Typically, master active area 334 produces a variable high voltage depending on the amount of deflection imposed thereon.

The desired stiffness or damping for system 330 is controlled by variable stiffness/damping circuitry 336, which sets and changes an electrical state provided by control electronics in system 330 to provide the desired stiffness/ damping applied by slave active area 332. In this case, stiffness/damping circuitry 336 inputs a signal to master active area 334 that results in a desired voltage from master active area 334 based on its current deflection. In addition, stiffness/damping may circuitry 336 input a parameter to open loop control 338. Alternatively, if step-up or step-down circuitry is used to alter the voltage from master active area 334, circuitry 336 may input a signal to the step-up or step-down circuitry to permit voltage control.

As slave active area 332 deflects, its changing voltage causes charge to move between slave 332 and buffer capacitor 340. Thus, externally induced expansion and contraction of slave active area 332, e.g., from a vibrating mechanical interface, causes charge to flow back and forth between slave active area 332 and buffer capacitor 340 through open loop control 338. The rate and amount of charge moved to or from slave 332 depends on the properties of buffer capacitor 340, the voltage applied to slave 332, any additional electrical components in the electrical circuit (such as a resistor used as open loop control 338), the mechanical configuration of slave 332, and the forces applied to or by slave 332. In one embodiment, buffer capacitor 340 has a voltage substantially equal to that of slave 332 for zero displacement of slave 332, the voltage of system 330 is set by master active area 334, and open loop control 338 is a wire; resulting in substantially free flow of charge between slave 332 and buffer capacitor 340 for deflection of slave 332.

Open loop control 338 provides a passive (no external energy supplied) dynamic response for stiffness applied by slave 332. Namely, the stiffness provided by slave 332 may be set by the electrical components included in system 330, such as the control electronics and voltage provided by master active area 334, or by a signal from control circuitry 336 acting upon one of the electrical components. Either way, the response of slave 332 is passive to the external mechanical deflections imposed on it. In one embodiment, open loop control 338 is a resistor. One can also set the resistance of the resistor to provide an RC time constant relative to a time of interest, e.g., a period of oscillation in the mechanical system that the transducer is implemented in. In one embodiment, the resistor has a high resistance such that the RC time constant of open loop control 338 and slave 332 connected in series is long compared to a frequency of interest. In this case, the slave 332 has a substantially constant charge during the time of interest. A resistance that produces an RC time constant for the resistor and the slave in the range of about 5 to about 30 times the period of a frequency of interest may be suitable in this case. An RC time constant in the range of about 2 to about 100 times the frequency of interest is suitable for some applications. An RC time constant in the range of about 10 to about 20 times the frequency of interest may be suitable for other applications. For applications including cyclic motion, increasing the RC time constant much greater than the mechanical periods of interest allows the amount of charge on electrodes of slave 332 to remain substantially constant during one cycle. In cases where slave 332 is used for damping, a resistance that produces an RC time constant for the resistor and the transducer in the range of about 0.1 to about 4 times the period of a frequency of interest may be suitable. As one of skill in the art will appreciate, resistances used for the resistor may vary based on application, particularly with respect to the frequency of interest and the size (and therefore capacitance C) of the slave 332.

In one embodiment of a suitable electrical state used to control stiffness and/or damping using open loop techniques, the control electronics apply a substantially constant charge to electrodes of slave 332, aside from any electrical imperfections or circuit details that minimally affect current flow. The substantially constant charge results in an increased stiffness for the polymer that resists deflection of slave 332. One electrical configuration suitable for achieving substantially constant charge is one that has a high RC time constant, as described. When the value of the RC time constant of open loop control 338 and slave 332 is long compared to the frequency of interest, the charge on the electrodes for slave 332 is substantially constant. Variable stiffness and damping systems are further described in commonly owned U.S. patent application Ser. No. 10/053, 511, which is incorporated herein by reference for all purposes.

Energy from an active area may also be used to power an electroactive polymer sensor. For example, a master active area may be disposed in a shoe to generate electrical energy that is used to power a slave active area configured as a sensor. A slave active area configured as a sensor measures a change in a parameter of an object being sensed. Typically, the parameter change induces deflection in the slave, which is converted to an electrical change output by electrodes attached to the slave. Many methods for applying mechanical or electrical energy to deflect the polymer are possible. Typically, the sensing of electrical energy from a slave uses electronics of some type. For instance, a minimum amount of circuitry is needed to detect a change in the electrical state across the electrodes.

Figure 5D:
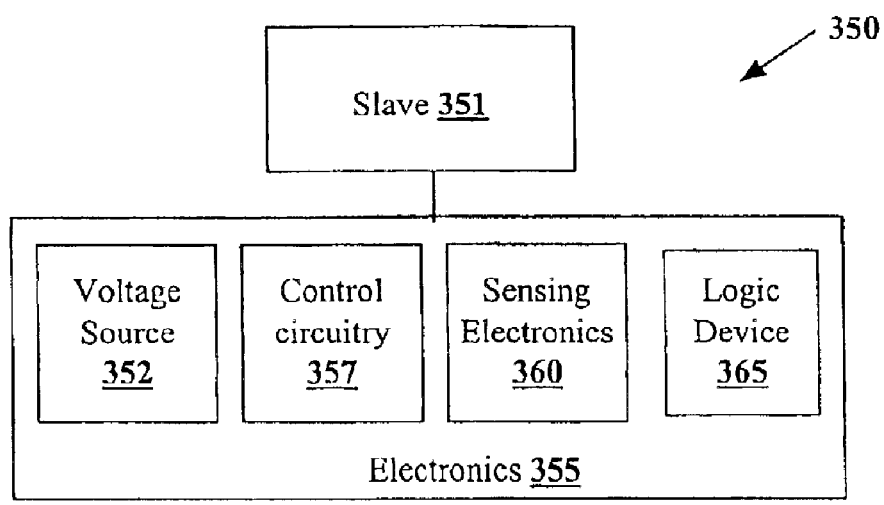
FIG. 5D is a block diagram of a sensor employing a slave active area according to one embodiment of the present invention.

FIG. 5D is a schematic of a sensor 350 employing a slave active area 351 according to one embodiment of the present invention. As shown in FIG. 5D, sensor 350 comprises slave active area 351 and various electronics 355 in electrical communication with the electrodes of slave 351. Electronics 355 are designed or configured to add, remove, and/or detect electrical energy from slave 351. While many of the elements of electronics 355 are described as discrete units, it is understood that some of the circuit functions may be integrated. For instance, one integrated circuit may perform the functions of both the logic device 365 and the charge control circuitry 357.

In one embodiment, the slave 351 is prepared for sensing by initially applying a voltage between its electrodes. In this case, a voltage, $V_I$, is provided by the master active area 352. Generally, $V_1$ is less than the voltage required to actuate slave 351. In some embodiments, a low-voltage battery may supply voltage, $V_I$, in the range of about 1–15 Volts. In any particular embodiment, choice of the voltage, $V_I$, may depend on a number of factors such as the polymer dielectric constant, the size of the polymer, the polymer thickness, environmental noise and electromagnetic interference, compatibility with electronic circuits that might use or process the sensor information, etc. The initial charge is placed on slave 351 using electronics control sub-circuit 357. The electronics control sub-circuit 357 may typically include a logic device such as single chip computer or microcontroller to perform voltage and/or charge control functions on slave 351. The electronics control sub-circuit 357 is then responsible for altering the voltage provided by master 352 to initially apply the relatively low voltage on slave 351.

Sensing electronics 360 are in electrical communication with the electrodes of slave 351 and detect the change in electrical energy or characteristics of slave 351. In addition to detection, sensing electronics 360 may include circuits configured to detect, measure, process, propagate, and/or record the change in electrical energy or characteristics of slave 351. As described above, electroactive polymer transducers of the present invention may behave electrically in several ways in response to deflection of the electroactive polymer transducer. Correspondingly, numerous simple electrical measurement circuits and systems may be implemented within sensing electronics 360 to detect a change in electrical energy of slave 351. For example, if slave 351 operates in capacitance mode, then a simple capacitance bridge may be used to detect changes in slave 351 capacitance. In another embodiment, a high resistance resistor is disposed in series with slave 351 and the voltage drop across the high resistance resistor is measured as the slave 351 deflects. More specifically, changes in slave 351 voltage induced by deflection of the electroactive polymer are used to drive current across the high resistance resistor. The polarity of the voltage change across resistor then determines the direction of current flow and whether the polymer is expanding or contracting. Resistance sensing techniques may also be used to measure changes in resistance of the polymer included in the slave or changes in resistance of the electrodes included in the slave. Some examples of these techniques are described in commonly owned patent application Ser. No. 10/007,705, which was previously incorporated by reference.

7. Electroactive Polymer Devices

The deflection of an electroactive polymer can be used in a variety of ways to produce or receive mechanical energy. Generally, electroactive polymers of the present invention may be implemented in a variety of sensors, actuators and generators—including conventional sensors, actuators and generators retrofitted with an electroactive polymer and custom sensors, actuators and generators specially designed for one or more active areas. Conventional actuators include extenders, bending beams, stacks, diaphragms, etc. Several exemplary devices suitable for use with as a sensor, actuator or generator will now be discussed. Additional actuators suitable for use with various embodiments of the present invention are described in copending U.S. patent application Ser. No. 09/619,848, which is incorporated by reference herein for all purposes.

Figure 6A:
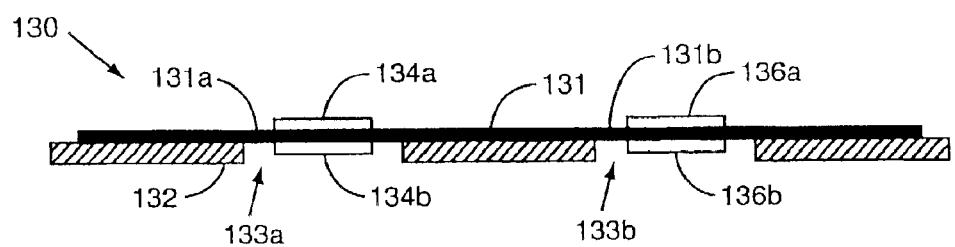
FIGS. 6A and 6B illustrate a device comprising a monolithic transducer for converting between electrical energy and mechanical energy in accordance with another embodiment of the present invention.

FIG. 6A illustrates a cross-sectional side view of a monolithic diaphragm device 130 comprising a monolithic polymer 131 before deflection in accordance with one embodiment of the present invention. The polymer 131 is attached to a frame 132. The frame 132 includes apertures 133*a* and 133*b* that allow deflection of polymer portions 131*a* and 131*b* perpendicular to the area of the apertures 133*a* and 133*b*, respectively. The diaphragm device 130 comprises electrodes 134*a* and 134*b* attached on either side of the portion 131*a* to provide a voltage difference across the portion 131*a*. Electrodes 136*a* and 136*b* are deposited on either side of the portion 131*b* to provide or receive a voltage difference across the portion 131*b*. The electrodes 134 and 136 are compliant and change shape with polymer 131 as it deflects. In the voltage-off configuration of FIG. 2A, polymer 131 is stretched and secured to frame 132 with tension to achieve pre-strain.

Figure 6B:
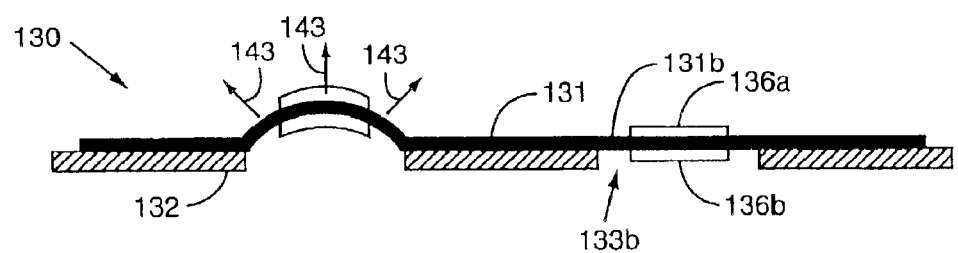

Using electrodes 134 and 136, portions 131*a* and 131*b* are capable of independent deflection. For example, upon application of a suitable voltage between electrodes 134*a* and 134*b*, portion 131*a* expands away from the plane of the frame 132, as illustrated in FIG. 2B. Each of the portions 131*a* and 131*b* is capable of expansion in both perpendicular directions away from the plane. In one embodiment, one side of polymer 131 comprises a bias pressure that influences the expansion of the polymer film 131 to continually actuate upward in the direction of arrows 143 (FIG. 6B). In another embodiment, a swelling agent such as a small amount of silicone oil is applied to the bottom side to influence the expansion of polymer 131 in the direction of arrows 143. The swelling agent allows the diaphragm to continually actuate in a desired direction without using a bias pressure. The swelling agent causes slight permanent deflection in one direction as determined during fabrication, e.g. by supplying a slight pressure to the bottom side when the swelling agent is applied.

Either of the active areas in diaphragm device 130 may be used as a master or slave. If one active area is used as a master in generation, a pressure, such as a fluid pressure, acts as mechanical input to the diaphragm device 130 on one side to stretch polymer 131 in the vicinity of apertures 133*a* and 133*b*. After the stretch, a voltage difference is applied between electrodes 134 while portions 131*a* is stretched. The resulting change in electric field provided to electrodes 134 is less than the electric field needed to further deflect polymer 131*a*. Similarly, a voltage difference is applied between electrodes 136 while portion 131*b* is stretched. Releasing the pressure allows portions 131*a* and 131*b* to contract and increase the stored electrical energy on electrodes 134 and 136. Electrical energy generated by the active areas in diaphragm device 130 may be provided to another device or polymer for example. Alternately, electrical energy generated by one of the active areas may be provided to the other active area.

Figure 6C:
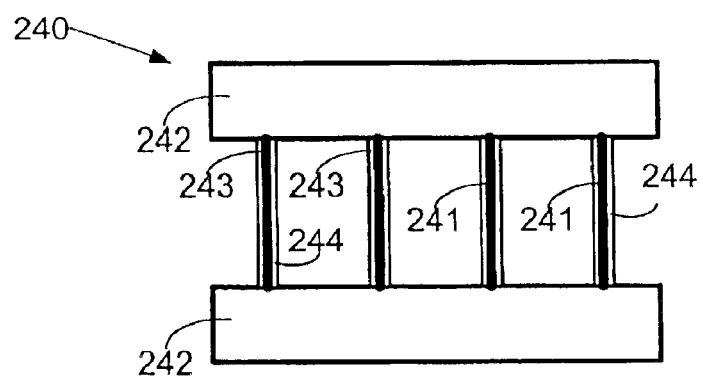
FIG. 6C illustrates a cross-sectional side view of a multilayer device in accordance with one embodiment of the present invention.

A collection of electroactive polymers or devices may be mechanically linked to form a larger device with scaled performance, e.g. force and/or displacement. By using a small electroactive polymer transducer as a base unit in a collection, actuation, generation, and stiffness and damping control may be scaled according to an application. FIG. 6C illustrates cross-sectional side view of a multilayer device 240 for providing stiffness and damping control in accordance with one embodiment of the present invention. The multilayer device 240 includes four polymers 241 arranged in parallel and each attached to a rigid member 242 such that they have the same deflection. Electrodes 243 and 244 are deposited on opposite surfaces of each polymer 241 and are in electrical communication such that they provide independent electrical control for active areas on each polymer 241. Rigid members 242 allow mechanical interface between polymers 241 and an external mechanical load.

The multilayer device 240 provides cumulative actuation, generation, and stiffness and damping control of the individual polymer layers 241. In one embodiment, electrodes 243 and 244 and their associated control electronics are configured to provide synchronous control for polymers 241. In another embodiment, electrodes 243 and 244 and their associated control electronics are configured to provide separate control for each polymer 241. In this manner, one may use simple on/off voltage control to independently provide actuation or stiffness control for each polymer 241. This binary independent on/off control allows a user relatively simple graduated actuation or stiffness control for device 240 since the effective stiffness is the sum of the stiffnesses of the individual polymer elements 241.

Figure 6D:
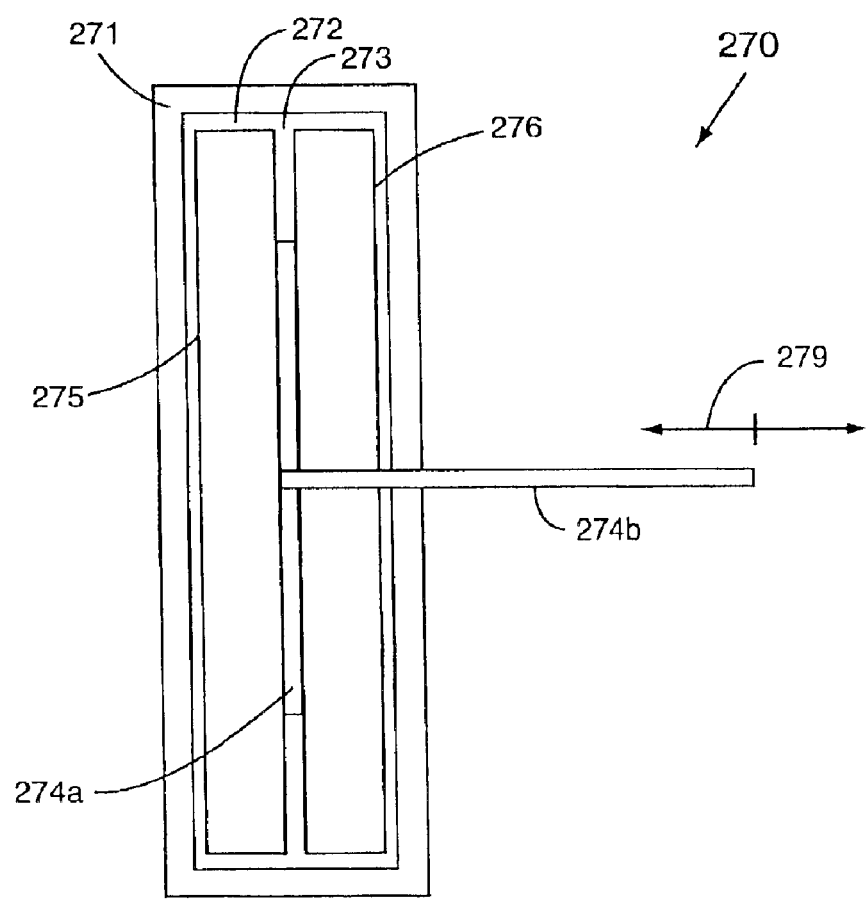
FIG. 6D illustrates a stretched film device in accordance with one embodiment of the present invention.

FIG. 6D illustrates a stretched film device 270 in accordance with another embodiment of the present invention. The stretched film device 270 comprises a rigid frame 271 having a hole 272. The perimeter of a monolithic electroactive polymer 273 is attached in tension to the frame 271 and spans the hole 272. A substantially rigid member 274 includes two segments 274a and 274b. The first segment 274a is attached to the center of the polymer 273. The second segment 274b provides mechanical output corresponding to deflection of the polymer 273.

Compliant electrode pairs 275 and 276 are patterned on both opposing surfaces of the polymer 273 and on the left and right sides of the first segment 274a, respectively. The second segment 274b is capable of motion assisted by deflection of the polymer in response to a change in electric field provided by electrode pairs 275. When the electrode pair 275 is actuated, a portion of the polymer 273 between, and in the vicinity of, the electrode pair 275 expands relative to the rest of the polymer 273 to move the second segment 274b to the right. Conversely, when the electrode pair 276 is actuated, a second portion of the polymer 273 affected by the electrode pair 276 expands relative to the rest of the polymer 273 and pushes the second segment 274b to move to the left. Alternating actuation of the electrodes 275 and 276 provides a total stroke 279 for the second segment 274b.

One variation of the stretched film device 270 includes adding an anisotropic prestrain to the polymer such that the polymer has high pre-strain (and stiffness) in the direction perpendicular to the rigid bar displacement. This increases the stroke 279. The first segment 274a can be different lengths depending on the size of the polymer 273 and its prestrain. In one embodiment, the first segment 274a is about 75% of the length of the hole 272 along the direction of the central attachment (perpendicular to stroke 279). When acting as a generator or sensor, the second segment 274b is capable of motion that causes a change in electric field in the polymer associated with electrode pairs 275.

Figure 6E:
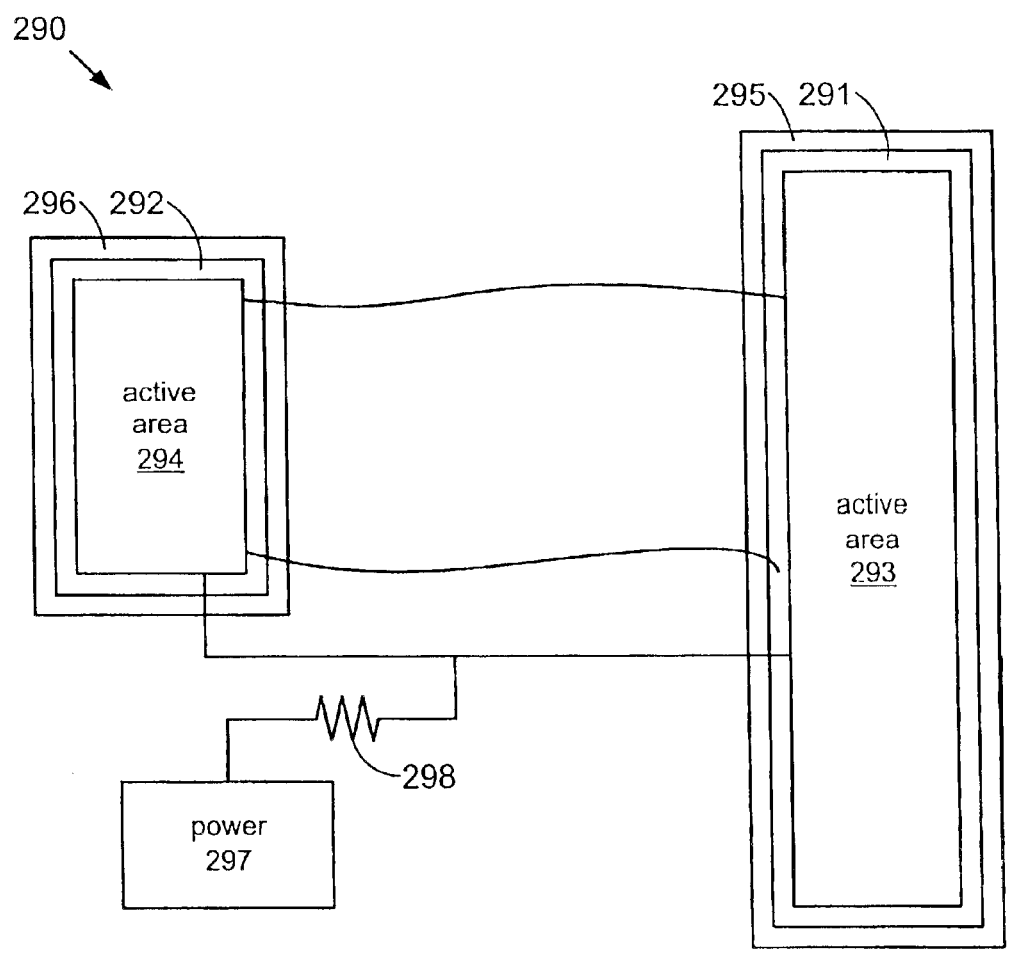
FIG. 6E illustrates a master/slave electroactive polymer system in accordance with a specific embodiment of the present invention.

In a specific embodiment, a master/slave electroactive polymer system 290 uses two separate electroactive polymers 291 and 292, as illustrated in FIG. 6E. Polymer 291 includes active area 293. Polymer 292 includes active area 294. Either active area can be a master or slave. The two polymers 291 and 292 are on different frames 295 and 296, respectively, and thus have no mechanical connection. The two active areas 293 and 294 are electrically connected in parallel using wires, and connected to a power supply 297 through a resistor 298. Resistor 298 allows electrical energy to flow at a trickle to charge active areas 293 and 294 up, but prevents power supply 297 from reacting to any sufficiently fast change in voltage. "Sufficiently fast" means that the power supply cannot supply a significant amount of charge during the change. For example, if resistor 298 is chosen to have a value R, and C is the smallest capacitance of either polymer 291 or 292, then changes much faster than RC will be sufficiently fast so that significant amounts of charge cannot flow across resistor 298 during the change. This criterion is only a rough guide, however, since if the larger capacitance polymer is being deflected as the master then the changes can be slower, or if full response is not needed then a slower change may be acceptable. When the active area 293 expands, active area 294 contracts, and vice versa. In a specific embodiment, active area 293 is about 6×26 cm in area and 0.005 cm thick, active area 294 is about 6×9 cm and 0.005 cm thick, the polymers have a dielectric constant of 4–5 (typical of some acrylic elastomers) and resistor 298 is 120 megaohm. For these numbers, the minimum RC time constant is roughly 0.5 seconds, so change that are much faster than 0.5 s will be transmitted well from master to slave. Of course, slower changes may also be used if a partial response is acceptable, or if the larger polymer (RC is roughly 1.5 s for the larger polymer) is used as the master.

Other configurations are possible. One worth mentioning is that instead of connecting the master-slave in parallel, they may be connected in series instead. In this case, when the master is stretched, the slave expands as well. Thus, in the parallel case the master and slave move oppositely, whereas in the series case they move in the same direction. The conditions for the voltage experienced by the master and slave can be determined using well-known formulas for series capacitors, the only difference being that the capacitance can take on different values. For the series arrangement one can use a constant voltage power supply supplying a voltage $V_B$ to the series polymers. The proportion of the voltage $V_B$ across each polymer can then be calculated based on their relative capacitance.

8. Applications

Master/slave electroactive polymer systems of the present invention have numerous applications. As the present invention includes electroactive polymer systems that may be implemented in both the micro and macro scales, implemented in sensor, actuator and generator applications where parameter detection, mechanical output and/or energy generation is desirable, and implemented with a wide variety of master/slave designs, the present invention finds use in a broad range of applications. These applications include actuators, motors, generators, sensors, robotics, footwear, toys, micro-actuator applications and pumps. Provided below are several exemplary applications for some of the transducers and devices described above. The exemplary applications described herein are not intended to limit the scope of the present invention. As one skilled in the art will appreciate, transducers of the present invention may find use in countless applications requiring conversion between electrical and mechanical energy.

In one embodiment, master/slave systems of the present invention are implemented in a glove or computer input device that includes multiple active areas that detect or respond to linear strain of portions of the glove in the immediate area of each transducer. Each active area may be coupled to the glove using glue or integrated into the glove material. Such a device is useful for virtual reality applications, microsurgical applications, and remote surgical applications for example. In a surgical application for example, a physician wears a glove whose movements control the motion of a robotic hand via a master/slave design.

Figure 7A:
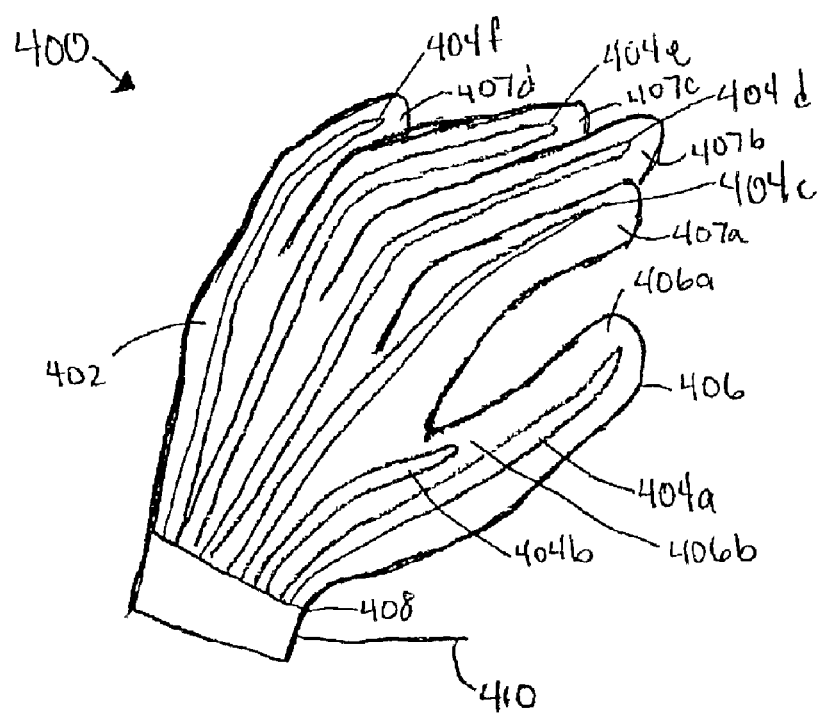
FIG. 7A illustrates a master/slave system where a glove comprises numerous master active areas in accordance with another specific embodiment of the present invention.

FIG. 7A illustrates a master/slave system where a glove 400 comprises numerous master active areas in accordance with another specific embodiment of the present invention. Glove 400 fits onto a person's hand and includes a stretchable fabric 402 that provides flexible structure and also acts as an electroactive polymer. Active areas 404 are defined by electrodes patterned on the outside (shown) and inside (not shown) surfaces of rubberized fabric 402. Thus, rubberized fabric 402 is a monolithic polymer and glove 400 comprises a master active array disposed on a single electroactive polymer.

Deflection of active areas 404 corresponding to hand movements generate electrical changes in the immediate area of the active areas 404. For example, active area 404a extends from a wrist 408 to the distal end 406a of thumb 406. Bending of thumb 406 stretches active area 404a and generates electrical energy changes within the active area 404a (with electrical conditioning on the electrodes). Wires 410 extend from wrist portion 408 and are in electrical communication with electrodes for each active area 404 of glove 400. Wires 410 provide electrical communication between active areas 404 and external communication electronics. The communication electronics are associated with multiple slave active areas on a robotic hand whose movements mimic glove 400. The robotic hand may be used in teleorobotic and surgical applications, or anywhere that force or haptic feedback needs to be communicated electrically such as to allow a user in one location to feel what the wearer of the glove is feeling. for example. Thus, when active area 404a bends, the matching motion is produced in the associated slave active area for the robotic hand.

Active area 404b extends from wrist 408 to an intermediate portion 406b of thumb 406. Deflection of active area 404b allows motion of intermediate portion 406b of thumb 406 to be transferred to the slave device; thus providing matching motion for the distal end 406a and the intermediate joint of a user's thumb moving within glove 400. Active areas 404c–f extend from wrist 408 to a distal end of each finger 407a–d, respectively, and provide master/slave guided motion between each finger in glove 400 and the slave device. This guided motion allows the wearer to create complex hand motions for the slave using his or her own hand, for example.

Active areas 404a–f are shown in FIG. 7A as elongated active areas. They can, however, be configured in a variety of patterns to emphasize different motions and increase the fidelity of the slave motion relative to the master. One can, for example, use more, but smaller, active areas where each active area corresponds to a hand joint. The system in FIG. 7A can also be configured with two basic types of communication electronics relative to the slave. In one configuration, the active areas of the master act mainly as sensors and do not supply substantial power to the slave. In this case, the communication electronics could be voltage amplifiers that amplify the power sent to the slave based on signals from the master. Alternately, a simpler configuration is to have slave active areas in series with corresponding master areas. As noted previously, placing master-slave active areas in parallel with a fixed bias voltage makes the slave actuate in the same direction as the master.

Master/slave electroactive polymer systems of the present invention are also well-suited for use in footwear such as shoes. As the term is used herein, footwear generally refers to any covering or attachment to a foot. This may include walking shoes; running shoes; athletic shoes for a particular sport such as soccer shoes, football shoes, tennis shoes; fashion footwear including women's shoes of varying shapes and designs; sandals; snowshoes; boots such as work boots; impact protection footwear; ski and snowboarding boots; and so on. Common parts of footwear may include a sole, heel, front toe portion, arch, tongue, ankle support or high top, etc. One of skill in the art will recognize the wide array of footwear currently available, and the present invention is not intended to be limited to any particular type of footwear. The present invention may also include foot coverings such as socks, which are particularly useful for sensing applications.

In one embodiment, a generator active area may be configured as the master portion of the master/slave system to provide electrical energy resulting from human bipedal motion. The slave electroactive polymer may be disposed in a shoe and use electrical energy provided by the master. For example, the slave may be disposed cylindrically around the ankle of a person wearing the shoe and configured to automatically increase in stiffness or tightness of the shoe in response to electrical energy generated by the master, and transferred by communication electronics between the master and slave. The master may be employed in the heel to generate electrical energy when the heel strikes the ground, for example. In this manner, stiffness support for the person's ankle is provided when the person's heel strikes the ground. The communication electronics may alter the energy as produced by the master as required by the desired stiffness of the shoe. For example, they may alter the time discontinuous nature of the energy produced by repeated heel strikes such that support for the ankle is more consistent over time. Alternately, the master may be placed in a top bending portion of the shoe to recover plastic energy generated by bipedal motion in this area, such as the region between the top of the shoe and the shin. Again, communication electronics may supply this energy to another portion of the shoe and alter the energy as produced by the master as required by needs of the slave.

Figure 7B:
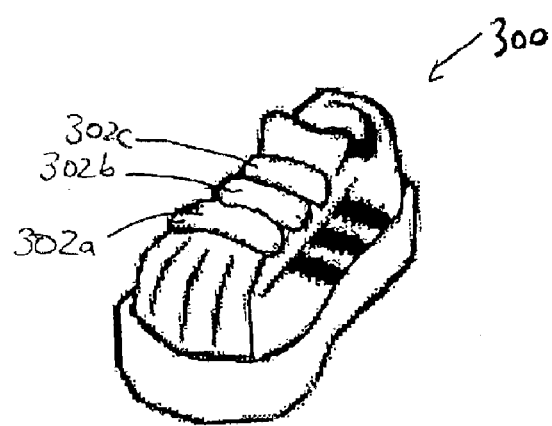
FIG. 7B illustrates multiple linear transducers configured to vary the stiffness of a top portion of shoe in accordance with a specific embodiment of the present invention.

Thus, a master/slave electroactive polymer system may be configured to provide variable stiffness for one or more portions of a shoe in response to electrical energy provided by the master, such as shoe 300 as shown in FIG. 7B. This may include varying the stiffness of different parts, such as the sidewalls of hightop footwear or the upper portion of footwear affected by laces of footwear 300. The stiffness provided by the slave may be altered for different times of usage. For example, shoes for daily wear may have a heel that decreases in stiffness when the shoe is not being used, e.g., when a person is relaxing at a desk, but increases when the shoe is being used, e.g., for locomotion. Air or fluid filled sacs having an exterior comprising an electroactive polymer that varies in stiffness may be disposed in a heel to vary stiffness as desired. As transducers of the present invention may be manufactured in a wide variety of custom shapes and designs, the configuration of an electroactive polymer transducer in a shoe will vary with design, as one of skill in the art will appreciate. Different portions of the shoe other than the heel may relax and increase in stiffness in this manner. In a specific embodiment, a transducer is employed to vary the stiffness provided by an insole disposed in the shoe. In the embodiment shown in FIG. 7B transducers 302*a–c* are disposed on the upper portion of shoe 300 to vary the stiffness across the top portion of the shoe or to tighten the shoe. Stiffness of various portions of the shoe may also vary based on user preferences or sensed features of the environment, e.g., stiffness is controlled depending on ground conditions such as sand, asphalt, rocks, etc., or may vary based on the mode of locomotion, e.g., a different stiffness for walking than for running or resting. It is well-known that tuning the stiffness and damping of a shoe to accommodate for changes in stiffness and damping of the environment experienced while walking or running, for example, can enhance the efficiency of locomotion.

Electrical power for the slave may come from a variety of master sources. In one embodiment, the master disposed in the footwear provides at least partial power to actuate an electroactive polymer. The mechanical power may be generated during heel strike (to expand a polymer) and relaxation process may correspond to a person lifting their foot after it has struck the ground. As the polymer relaxes, the voltage of the charge on the polymer film is increased. The increase in charge's electrical energy, as indicated by its higher voltage, on the polymer film is harvested to generated electrical energy that is provided to the slave.

Slave electroactive polymers disposed in a heel of the shoe may be used to vary the stiffness of the heel. The stiffness may then be controlled or manipulated to affect locomotion for a person, such as to improve walking or running. Stiffness of the polymers may then be tuned to achieve a particular performance of the footwear desirable to an application or the characteristics of the wearer, such as a high stiffness for running or for use with a heavier person.

Alternately, a shoelace arrangement may be established in which the shoelace is replaced with a device that incorporates an electroactive polymer actuator acting as a slave that tightens the footwear around the person's foot in response to electrical energy provided by the master. Again, the master may be disposed in the heel of the footwear and produce electrical resulting from locomotive energy of the person. In one embodiment, the shoe tightens and increases stiffness for the footwear during impact of the foot with the ground or substantially thereafter. In another embodiment, control electronics and electrical energy storage mechanisms in electrical communication with electrodes of the slave and master store electrical energy produced from one or more impacts of the foot. The electrical energy may be saved for subsequent actuation of the slave. For example, the electrical energy may be saved and output to produce a continuous increase in stiffness or tightening of the footwear for prolonged time corresponding to an activity of the footwear (e.g., running or walking for a given period of time).

As noted earlier, the slave motion can be in the same direction as the master (e.g. series connection; expanding master expands slave) or in the opposite direction as the master (e.g. parallel connection; expanding master contracts the slave). Multiple master areas and/or slave areas can also be used. Systems such as this have many applications. More complex configurations, that might be referred to as polymer or muscle "logic", are indeed possible. For example, two "masters" A and B, and a slave C may be employed. With high and low sides connected in parallel, C responds only when there is a net change in active area on the masters. That is, if A expands but B contracts at the same rate, the high side voltage doesn't change so C doesn't change. This configuration might be likened to an "AND" gate. One could also do an "exclusive OR" gate by connecting the high sides of A and B to the two opposite electrodes on C. Then C only responds when there is a voltage difference between the high sides of A and B (e.g. A is expanded when B is contracted or vice versa). One could also make a flip-flop using a master-slave by inserting a simple diode between master and slave (C expands when A contracts, but when A is expanded again the diode prevents pulling the charge backward).

The master/slave systems of the present invention are also useful for remote sensor applications requiring their own power. In one embodiment, a master receives mechanical energy from a change in a parameter being sensed or energy from the environment around the master, and converts the energy to electrical energy within the master/slave system. Either the master or the slave, or a combination thereof, may then be used as electroactive polymer sensor.

9. Conclusion

While this invention has been described in terms of several preferred embodiments, there are alterations, permutations, and equivalents that fall within the scope of this invention which have been omitted for brevity's sake. For example, although the present invention has been described in terms of several specific electrode materials, the present invention is not limited to these materials and in some cases may include air as an electrode. In addition, although the present invention has been described in terms of several preferred polymer materials and geometries, the present invention is not limited to these materials and geometries. It is therefore intended that the scope of the invention should be determined with reference to the appended claims.

What is claimed is:

1. A device for converting between electrical and mechanical energy, the device comprising:
    a first active area that converts between electrical energy and mechanical energy, the first active area comprising a first portion of at least one electroactive polymer and at least two first active area electrodes in electrical communication with the first portion;
    a second active area that converts between electrical energy and mechanical energy, the second active area comprising a second portion of the at least one electroactive polymer and at least two second active area electrodes in electrical communication with the second portion; and
    communication electronics, in electrical communication with the first active area and in electrical communication with the second active area, that transfer at least a portion of an electrical energy change from one of the first active area and the second active area to the other of the first active area and the second active area.

2. The device of claim 1 wherein the communication electronics are passive.

3. The device of claim 2 wherein the communication electronics comprise a wire.

4. The device of claim 1 wherein the communication electronics introduce a time delay before transferring the portion of the electrical energy change between the first active area and the second active area.

5. The device of claim 1 wherein the communication electronics comprise a capacitor.

6. The device of claim 1 wherein the communication electronics comprise a diode.

7. The device of claim 6 wherein the diode prevents backflow of current from the other of the first active area and the second active area.

8. The device of claim 7 wherein the diode allows electrical energy to accumulate in the other of the first active area and the second active area.

9. The device of claim 1 further comprising conditioning electronics in electrical communication with the at least two first or second active area electrodes and designed or configured to add or remove electrical energy from the at least two first or second active area electrodes.

10. The device of claim 1 wherein the communication electronics provide electrical energy generated by one of the first active area and the second active area to the other of the first active area and the second active area.

11. The device of claim 1 wherein the first active area is configured to generate electrical energy in response to external deflection and the communication electronics provide at least a portion of the generated electrical energy to the second active area.

12. The device of claim 11 wherein the second active area uses the portion of electrical energy to produce mechanical energy.

13. The device of claim 1 wherein the first active area and second active area are configured to form a logic function.

14. The device of claim 1 wherein the first or the second active area is configured for one of actuation, generation, sensing, or changing the stiffness for a portion of the device.

15. The device of claim 1 further comprising one or more mechanical transmission mechanisms that are designed or configured to receive external mechanical energy and to transfer a portion of the external mechanical energy to the first active area or the second active area, wherein the transferred portion of the mechanical energy results in a deflection in the active area receiving the external mechanical energy.

16. The device of claim 15 wherein the one or more mechanical transmission mechanisms are designed or configured to receive biologically-generated mechanical energy.

17. The device of claim 1 wherein the electroactive polymer is a dielectric elastomer.

18. The device of claim 17 wherein the dielectric elastomer is pre-strained.

19. The device of claim 1 wherein the polymer has an elastic modulus below about 100 MPa.

20. The device of claim 1 further comprising a substantially rigid member coupled to a third portion of the at least one electroactive polymer.

21. The device of claim 1 wherein one of the first and the second active areas is included in footwear.

22. The device of claim 1 wherein the at least one electroactive polymer is a monolithic polymer and the first and second active area are disposed on the monolithic polymer.

23. The device of claim 1 wherein the first active area and the second active area are electrically connected in series.

24. The device of claim 11 wherein the communication electronics are passive.

25. The device of claim 11 wherein the communication electronics introduce a time delay before transferring electrical energy between the first active area and the second active area.

26. The device of claim 11 wherein the communication electronics comprise a diode.

27. The device of claim 26 wherein the diode prevents backflow of current from the second active area to the first motive area.

28. The device of claim 27 wherein the diode allows electrical energy to accumulate in the second active area.

29. The device of claim 11 further comprising conditioning electronics in electrical communication with the at least two first active area electrodes and designed or configured to add or remove electrical energy from the at least two first active area electrodes.

30. The device of claim 11 further comprising one or more mechanical transmission mechanisms that are designed or configured to receive mechanical energy and to transfer a portion of the mechanical energy to the first portion, wherein the transferred portion of the mechanical energy results in a deflection in the first portion.

31. The device of claim 30 wherein the one or more transmission mechanisms are designed or configured to receive biologically-generated mechanical energy.

* * * * *